(12) United States Patent
Parker

(10) Patent No.: US 11,938,320 B2
(45) Date of Patent: Mar. 26, 2024

(54) ELECTRODE TO NERVE DISTANCE ESTIMATION

(71) Applicant: Saluda Medical Pty Ltd, Macquarie Park (AU)

(72) Inventor: John Louis Parker, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 145 days.

(21) Appl. No.: 17/121,545

(22) Filed: Dec. 14, 2020

(65) Prior Publication Data

US 2021/0162214 A1 Jun. 3, 2021

Related U.S. Application Data

(63) Continuation of application No. 15/561,960, filed as application No. PCT/AU2016/050263 on Apr. 8, 2016, now Pat. No. 10,894,158.

(30) Foreign Application Priority Data

Apr. 9, 2015 (AU) ................................ 2015901270

(51) Int. Cl.
*A61N 1/00* (2006.01)
*A61N 1/36* (2006.01)

(52) U.S. Cl.
CPC ..... *A61N 1/36062* (2017.08); *A61N 1/36067* (2013.01); *A61N 1/36139* (2013.01); *A61N 1/36075* (2013.01); *A61N 1/36185* (2013.01)

(58) Field of Classification Search
CPC ........................ A61N 1/36067; A61N 1/36062
(Continued)

(56) References Cited

U.S. PATENT DOCUMENTS 3,724,467 A 4/1973 Avery et al.
3,736,434 A 5/1973 Darrow
(Continued)

FOREIGN PATENT DOCUMENTS

AU 2013277009 B2 1/2016
CN 103648583 A 3/2014
(Continued)

OTHER PUBLICATIONS

"Percutaneous Lead Kit", St. Jude Medical Clinician's Manual, Models 3143, 3146, 3149, 3153, 3156, 3159, 3183, 3186, 3189, published Sep. 2016, 24 pages.
(Continued)

*Primary Examiner* — Nicole F Lavert
(74) *Attorney, Agent, or Firm* — Barnes & Thornburg LLP

(57) ABSTRACT

Estimating a nerve-to-electrode distance involves applying a stimulus from a stimulus electrode to a nerve. Neural measurements of at least one evoked compound action potential are obtained, and processed in order to estimate an originating state of stimulation exhibiting at least one characteristic defined by a single fibre size. A single fibre model is then applied to produce a measure of the nerve-to-electrode distance. Also provided for is estimation of a distribution of recruited fibres. Measurements of a compound action potential are obtained from sense electrodes spaced apart along a neural pathway. A conduction velocity of the compound action potential is determined from the latency between the measurements. From the conduction velocity a dominant recruited fibre diameter is determined. A rate of dispersion of the compound action potential between the sense electrodes is determined. From the rate of dispersion a distribution of diameters of the recruited fibre population is determined.

12 Claims, 20 Drawing Sheets

(58) Field of Classification Search
USPC .......................................................... 607/72
See application file for complete search history.

(56) References Cited

U.S. PATENT DOCUMENTS

| | | | |
|---|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndor et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,083,685 B2 | 12/2011 | Fagin et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,332,047 B2 | 12/2012 | Libbus et al. |
| 8,359,102 B2 | 1/2013 | Thacker et al. |
| 8,401,655 B2 | 3/2013 | De Ridder |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,588,929 B2 | 11/2013 | Davis et al. |
| 8,670,830 B2 | 3/2014 | Carlson et al. |
| 8,886,323 B2 | 11/2014 | Wu et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,110,270 B2 | 9/2021 | Parker et al. |
| 11,167,129 B2 | 11/2021 | Parker |
| 11,172,864 B2 | 11/2021 | Parker et al. |
| 11,179,091 B2 | 11/2021 | Karantonis et al. |
| 11,191,966 B2 | 12/2021 | Wah |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0116978 A1 | 6/2004 | Bradley |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0107674 A1 | 5/2005 | Parthasarathy et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0216064 A1 | 9/2005 | Heruth et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0129205 A1 | 6/2006 | Boveja et al. |

(56) References Cited

U.S. PATENT DOCUMENTS

| | | |
|---|---|---|
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0265489 A1 | 11/2007 | Borgerding et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0281594 A1 | 11/2009 | Wacnik et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1* | 2/2011 | Gerber ............... A61N 1/37247 703/11 |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0130802 A1 | 6/2011 | Libbus et al. |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0288391 A1 | 11/2011 | Rao et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0046407 A1 | 2/2014 | Ben-ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-Diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1* | 10/2014 | Parker ............... A61B 5/4836 600/554 |
| 2014/0324118 A1 | 10/2014 | Simon et al. |
| 2014/0350634 A1* | 11/2014 | Grill ............... A61N 1/36067 607/45 |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0032181 A1* | 1/2015 | Baynham ............ A61N 1/36071 607/46 |
| 2015/0051637 A1 | 2/2015 | Osorio |
| 2015/0126839 A1 | 5/2015 | Li et al. |
| 2015/0148869 A1 | 5/2015 | Dorvall, II et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1* | 12/2015 | Bornzin ............ A61N 1/36139 607/62 |
| 2015/0374999 A1 | 12/2015 | Parker |
| 2016/0082265 A1 | 3/2016 | Moffitt et al. |
| 2016/0082268 A1 | 3/2016 | Hershey et al. |

(56) References Cited

U.S. PATENT DOCUMENTS

| | | |
|---|---|---|
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0008373 A1 | 1/2021 | Single et al. |
| 2021/0016091 A1 | 1/2021 | Parker et al. |
| 2021/0121696 A1 | 4/2021 | Parker et al. |
| 2021/0162214 A1 | 6/2021 | Parker |
| 2021/0267518 A1 | 9/2021 | Parker et al. |
| 2021/0308449 A1 | 10/2021 | Parker |
| 2021/0315502 A1 | 10/2021 | Parker et al. |
| 2021/0379386 A1 | 12/2021 | Parker et al. |
| 2021/0387005 A1 | 12/2021 | Parker et al. |
| 2021/0387008 A1 | 12/2021 | Single |
| 2021/0393964 A1 | 12/2021 | Single et al. |
| 2022/0007987 A1 | 1/2022 | Huang et al. |
| 2022/0039724 A1 | 2/2022 | Parker et al. |
| 2022/0151535 A1 | 5/2022 | Parker et al. |
| 2022/0151536 A1 | 5/2022 | Karantonis et al. |
| 2022/0168574 A1 | 6/2022 | Wah |
| 2022/0249009 A1 | 8/2022 | Parker et al. |
| 2022/0287620 A1 | 9/2022 | Parker |

FOREIGN PATENT DOCUMENTS

| | | | |
|---|---|---|---|
| CN | 103654762 A | 3/2014 | |
| CN | 103842022 A | 6/2014 | |
| CN | 104411360 A | 3/2015 | |
| EP | 0219084 | 4/1987 | |
| EP | 1244496 A1 | 10/2002 | |
| EP | 0998958 B1 | 8/2005 | |
| EP | 2019716 A | 11/2007 | |
| EP | 2243510 A2 | 10/2010 | |
| EP | 2443995 A2 | 4/2012 | |
| EP | 2520327 A2 | 11/2012 | |
| EP | 2707095 A1 | 3/2014 | |
| EP | 3229893 A1 | 10/2017 | |
| JP | 2006504494 A | 2/2006 | |
| JP | 2009512505 A | 3/2009 | |
| JP | 2012524629 | 10/2012 | |
| JP | 2013500779 A | 1/2013 | |
| JP | 2013527784 A | 7/2013 | |
| JP | 2013536044 A | 9/2013 | |
| JP | 2014522261 A | 9/2014 | |
| JP | 2014523261 A | 9/2014 | |
| WO | 1983003191 A | 9/1983 | |
| WO | 1993001863 A1 | 2/1993 | |
| WO | 1996012383 A1 | 4/1996 | |
| WO | 2000002623 A1 | 1/2000 | |
| WO | 2002036003 A1 | 11/2001 | |
| WO | 2002038031 | 5/2002 | |
| WO | 2002049500 A2 | 6/2002 | |
| WO | 2002082982 A1 | 10/2002 | |
| WO | 2003028521 A2 | 4/2003 | |
| WO | 2003043690 | 5/2003 | |
| WO | 2003103484 | 12/2003 | |
| WO | 2004021885 A1 | 3/2004 | |
| WO | 2004103455 | 12/2004 | |
| WO | 2005032656 A1 | 4/2005 | |
| WO | 2005105202 A1 | 11/2005 | |
| WO | 2005122887 A2 | 12/2005 | |
| WO | 2006091636 A2 | 8/2006 | |
| WO | 2007050657 A1 | 5/2007 | |
| WO | 2007064936 A1 | 6/2007 | |
| WO | 2007127926 A2 | 11/2007 | |
| WO | 2007130170 A1 | 11/2007 | |
| WO | 2008004204 A1 | 1/2008 | |
| WO | 2008049199 A1 | 5/2008 | |
| WO | 2009002072 A2 | 12/2008 | |
| WO | 2009002579 A1 | 12/2008 | |
| WO | 2009010870 A2 | 1/2009 | |
| WO | 2009130515 A2 | 10/2009 | |
| WO | 2009146427 A1 | 12/2009 | |
| WO | 2010013170 A1 | 2/2010 | |
| WO | 2010044989 A2 | 4/2010 | |
| WO | 2010051392 A1 | 5/2010 | |
| WO | 2010051406 A1 | 5/2010 | |
| WO | 2010057046 A2 | 5/2010 | |
| WO | 2010124139 A1 | 10/2010 | |
| WO | 2010138915 A1 | 12/2010 | |
| WO | 2011011327 A1 | 1/2011 | |
| WO | 2011014570 A1 | 2/2011 | |
| WO | 2011017778 A1 | 2/2011 | |
| WO | 2011066477 A1 | 6/2011 | |
| WO | 2011066478 A1 | 6/2011 | |
| WO | 2011112843 A1 | 9/2011 | |
| WO | 2011119251 A2 | 9/2011 | |
| WO | 2011159545 A2 | 12/2011 | |
| WO | 2012016138 A1 | 2/2012 | |
| WO | 2012027252 A2 | 3/2012 | |
| WO | 2012027791 A1 | 3/2012 | |
| WO | 2012155183 A1 | 11/2012 | |
| WO | 2012155184 A1 | 11/2012 | |
| WO | 2012155185 A1 | 11/2012 | |
| WO | 2012155187 A1 | 11/2012 | |
| WO | 2012155188 A1 | 11/2012 | |
| WO | 2012155189 A1 | 11/2012 | |
| WO | 2012155190 A1 | 11/2012 | |
| WO | 2012162349 A1 | 11/2012 | |
| WO | WO-2012155185 A1 * | 11/2012 | ............. A61B 18/14 |
| WO | 2013063111 A1 | 5/2013 | |
| WO | 2013075171 A1 | 5/2013 | |
| WO | 2013116161 A1 | 8/2013 | |
| WO | 2014071445 A1 | 5/2014 | |
| WO | 2014071446 A1 | 5/2014 | |
| WO | 2014143577 A1 | 9/2014 | |
| WO | 2014150001 A1 | 9/2014 | |
| WO | 2015070281 A1 | 5/2015 | |
| WO | 2015074121 A1 | 5/2015 | |
| WO | 2015109239 A1 | 7/2015 | |
| WO | 2015143509 A1 | 10/2015 | |
| WO | 2015168735 A1 | 11/2015 | |
| WO | 2016011512 A1 | 1/2016 | |

(56) References Cited

FOREIGN PATENT DOCUMENTS

| | | | |
|---|---|---|---|
| WO | 2016048974 A1 | 3/2016 | |
| WO | 2016059556 A1 | 4/2016 | |
| WO | 2016077882 A1 | 5/2016 | |
| WO | 2016090420 A1 | 6/2016 | |
| WO | 2016090436 A1 | 6/2016 | |
| WO | 2016115596 A1 | 7/2016 | |
| WO | 2016161484 A2 | 10/2016 | |
| WO | 2016168798 A1 | 10/2016 | |
| WO | 2016191807 A1 | 12/2016 | |
| WO | 2016191808 A1 | 12/2016 | |
| WO | 2016191815 A1 | 12/2016 | |
| WO | 2017053504 A1 | 3/2017 | |
| WO | 2017142948 A1 | 8/2017 | |
| WO | 2017173493 A1 | 10/2017 | |
| WO | 2017210352 A1 | 12/2017 | |
| WO | 2017219096 A1 | 12/2017 | |
| WO | 2018080753 A1 | 5/2018 | |
| WO | 2018119220 A1 | 6/2018 | |
| WO | 2018160992 A1 | 9/2018 | |
| WO | 2018170141 A1 | 9/2018 | |
| WO | 2019178634 A1 | 9/2019 | |
| WO | 2019204884 A1 | 10/2019 | |
| WO | 2019231796 A1 | 12/2019 | |
| WO | 2020082118 A1 | 4/2020 | |
| WO | 2020082126 A1 | 4/2020 | |
| WO | 2020082128 A1 | 4/2020 | |
| WO | 2020087123 A1 | 5/2020 | |
| WO | 2020087135 A1 | 5/2020 | |
| WO | 2020124135 A1 | 6/2020 | |
| WO | 2021007615 A1 | 1/2021 | |

OTHER PUBLICATIONS

Extended European Search Report for European Application 18910394.8 Search Completed Oct. 7, 2021, dated Oct. 15, 2021, 8 pgs.
Extended European Search Report for European Application No. 16802238.2, dated Jan. 14, 2022, 7 Pgs.
Extended European Search Report for European Application No. 19793420.1, Search completed Dec. 6, 2021, dated Dec. 17, 2021, 9 Pgs.
International Search Report and Written Opinion for International Application No. PCT/AU2020/050725, Search completed Oct. 19, 2020, dated Oct. 19, 2020, 8 Pgs.
Parker et al., "Electrically evoked compound action potential recording in peripheral nerves", Bioeletron. Med., vol. 1, No. 1, 2018, pp. 71-83, ISSN 2059-1500.
Kent, "Characterization of Evoked Potentials During Deep Brain Stimulation in the Thalamus", Dissertation, Duke University. Retrieved from https://hdl.handle.net/10161/8195, 2013.
Australian Examination Report for Application No. 2019283936, dated Apr. 1, 2021, 7 pages.
International Search Report and Written Opinion for International Application No. PCT/AU2019/051385, Search completed Mar. 24, 2020, dated Mar. 24, 2020, 8 Pgs.
International Search Report for International Application No. PCT/AU2019/051151, International Filing Date Oct. 22, 2019, Search Completed Feb. 24, 2020, dated Feb. 24, 2020, 9 pgs.
International Search Report for International Application No. PCT/AU2019/051160, International Filing Date Oct. 23, 2019, Search Completed Jan. 28, 2020, dated Jan. 28, 2020, 13 pgs.
International Search Report for International Application No. PCT/AU2019/051163, International Filing Date Oct. 23, 2019, Search Completed Jan. 21, 2020, dated Jan. 31, 2020, 8 pgs.
International Search Report for International Application No. PCT/AU2019/051197, International Filing Date Oct. 30, 2019, Search Completed Jan. 21, 2020, dated Jan. 21, 2020, 15 pgs.
International Search Report for International Application No. PCT/AU2019/051210, International Filing Date Nov. 2, 2019, Search Completed Feb. 4, 2020, dated Feb. 4, 2020, 10 pgs.
Japanese Office Action for Application No. 2018-552138, dated Mar. 1, 2021, 7 pages with English translation.

"Evoke 12C Percutaneous Leads", Saluda Medical, specifications available in the "Evoke Surgical Guide", version 6, http://www.saludamedical.com/manuals/, retrieved May 2017.
Abrard et al., "A time—frequency blindsignal separation methodapplicable to underdetermined mixtures of dependent sources", Signal Processing 85 (2005) 1389-1403.
Bratta et al., "Orderly Stimulation of Skeletal Muscle Motor Units with Tripolar Nerve Cuff Electrode", IEEE Transactions on Biomedical Engineering, vol. 36, No. 8, 1989.
Casey et al., "Separation of Mixed Audio Sources by Independent Subspace Analysis", Mitsubishi Electric Research Laboratories (2001).
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Delgado et al., "Measurement and interpretation of electrokinetic phenomena", Pure Appl. Chem., 2005, vol. 77, No. 10, pp. 1753-1805.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Howell et al., "Evaluation of Intradural Stimulation Efficiency and Selectivity in a Computational Model of Spinal Cord Stimulation", Plos One, DOI:10.1371/journal.pone.0114938, Dec. 23, 2014.
Jang et al., "Single Channel Signal Separation Using Time-Domain Basis Functions", IEEE Signal Processing Letters, Jun. 2003, vol. 10, No. 6.
Jang et al., "A Maximum Likelihood Approach to Single-channel Source Separation", Journal of Machine Learning Research 4 (2003) 1365-1392.
Jones et al., "Scaling of Electrode—Electrolyte Interface Model Parameters in Phosphate Buffered Saline", IEEE Transactions on Biomedical Circuits and Systems, 2015, vol. 9, No. 3, pp. 441-448.
Laird-Wah, "Improving Spinal Cord Stimulation: Model-Based Approaches to Evoked Response Telemetry", UNSW, Aug. 2015.
Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.
Niazy et al., "Removal of FMRI environment artifacts from EEG data using optimal basis sets", NeuroImage 28 (2005) 720 - 737.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Peterson et al., "Stimulation artifact rejection in closed-loop, distributed neural interfaces", ESSCIRC, 42nd European Solid-State Circuits Conference, Lausanne, 2016, pp. 233-235.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.

(56) References Cited

OTHER PUBLICATIONS

Takahashi et al., "Classification of neuronal activities from tetrode recordings using independent component analysis", Neurocomputing, (2002), vol. 49, Issues 1-4, 289-298.
Zhang et al., "Automatic Artifact Removal from Electroencephalogram Data Based on A Priori Artifact Information", BioMed research international. 2015. 720450. Aug. 25, 2015 DOI: https://doi.org/10.1155/2015/720450.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.
Extended European Search Report for European Application No. 15789515.2, Search completed Dec. 4, 2017, dated Jan. 30, 2018, 7 Pgs.
International Preliminary Report on Patentability for International Application No. PCT/AU2018/050278, dated Sep. 29, 2020, 7 pgs.
International Preliminary Report on Patentability for International Application No. PCT/AU2019/050384, dated Oct. 27, 2020, 8 pgs.
International Search Report and Written Opinion for International Application No. PCT/AU2018/050278, Search completed Jun. 18, 2018, dated Jun. 18, 2018, 12 Pgs.
International Search Report and Written Opinion for International Application No. PCT/AU2019/050384, Search completed Jun. 25, 2019, dated Jun. 25, 2019, 15 Pgs.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 09 Pgs.
Extended European Search Report for European Application No. 14861553.7, Search completed Jun. 8, 2017, dated Jun. 19, 2017, 8 Pgs.
Extended European Search Report for European Application No. 14863597.2, Search completed Jun. 6, 2017, dated Jun. 13, 2017, 9 Pgs.
Extended European Search Report for European Application No. 15768956.3, Search completed Oct. 3, 2017, dated Oct. 10, 2017, 8 Pgs.
Extended European Search Report for European Application No. 16739680.3, Search completed Jun. 1, 2018, dated Jun. 12, 2018, 9 Pgs.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
Extended European Search Report for European Application No. 13853514.1, Search completed Jun. 8, 2016, dated Jun. 15, 2016, 07 Pgs.
International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2012/001441, Report dated May 27, 2014, 10 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, dated Nov. 15, 2011, 13 pgs.

(56) References Cited

OTHER PUBLICATIONS

International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 Pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16Pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
International Search Report and Written Opinion for International Application No. PCT/AU2017/050296, Search completed Jul. 28, 2017, dated Jul. 28, 2017, 10 Pgs.
International Search Report and Written Opinion for International Application No. PCT/AU2017/050647, Search completed Sep. 29, 2017, dated Sep. 29, 2017, 13 Pgs.
International Search Report and Written Opinion for International Application No. PCT/AU2015/050215, Search completed Jul. 30, 2015, dated Jul. 30, 2015, 8 Pgs.
International Search Report for Australian Application 2011901829 Search Completed Feb. 6, 2012, dated Feb. 7, 2012, 3pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
International Type Search Report for International Application No. AU 2015902393, Search completed May 16, 2016, dated May 16, 2016, 8 Pgs.
Japanese Office Action for Application No. 2017-546830, dated Feb. 20, 2020, 5 pages with English translation.
Japanese Office Action for Application No. 2017-553090, dated Mar. 16, 2020, 12 pages with English translation.
Japanese Office Action for Application No. 2018-513699, dated Jun. 8, 2020, 7 pages with English translation.
Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Office Action for Chinese Patent Application No. 201680020725.4, dated Mar. 16, 2020, 8 pgs.
Partial European Search Report for European Application No. 16775966.1, Search completed Oct. 26, 2018, dated Nov. 6, 2018, 11 Pgs.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
"Advanced Pain Therapy using Neurostimulation for Chronic Pain", Medtronic RestoreSensor clinical trial paper, Clinical summary, 2011-11, pp. 32.
"Battelle Neurotechnology—Moving Beyond The Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Alam et al., "Evaluation of optimal electrode configurations for epidural spinal cord stimulation in cervical spinal cord injured rats", Journal of Neuroscience Methods, Mar. 2015, 28 pgs.

(56) References Cited

OTHER PUBLICATIONS

Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Devergnas et al., A, "Cortical potentials evoked by deep brain stimulation in the subthalamic area", Frontiers in System Neuroscience, May 13, 2011, vol. 5, Article 30, 2011, doi: 10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N. et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge By Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Fagius, J. et al., "Sympathetic Reflex Latencies and Conduction Velocities in Normal Man", Journal of Neurological Sciences, 1980. vol. 47, pp. 433-448.

Falowski et al., "Spinal Cord Stimulation: an update", Neurotherapeutics: The Journal of the American Society for Experimental Neuro Therapeutics 5, No. 1, Jan. 2008, pp. 86-99.
Fisher, "F-Waves—Physiology and Clinical Uses", TheScientificWorldJournal, (2007) 7, pp. 144-160.
Franke et al., FELIX, "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs., http://www.jneuroengrehab.com/content/10/1/2.
George et al., "Vagus nerve stimulation: a new tool for brain research and therapy", Biological Psychiatry 47, No. 4, Feb. 15, 2000, pp. 287-295.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012)., In 16th Annual Meeting. Presented at the North American Neuromodulation Society, Las Vegas, NV, 2 pgs.
Gorman et al., "Neural Recordings For Feedback Control Of Spinal Cord Stimulation: Reduction of Paresthesia Variability.", 2013, In International Neuromodulation Society 11th World Congress, presented at the International Neuromodulation Society 11th World Congress, Berlin, Germany, 2 pgs.
Hallstrom et al., "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.
Harper et al., A. A., "Conduction Velocity is Related to Morphological Cell Type in Rat Dorsal Root Ganglion Neurones", J. Physiol, (1985), vol. 359, pp. 31-46.
He et al., "Perception threshold and electrode position for spinal cord stimulation", Pain, vol. 59, (1994), pp. 55-63.
Herreras, "Local Field Potentials: Myths and Misunderstandings", Frontiers in Neural Circuits, Dec. 15, 2016, vol. 10, Article 1101, 16 pgs., doi:10.3389/fncir.2016.00101.
Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.
Holsheimer et al., "Significance of the Spinal Cord Position in Spinal Cord Stimulation", Acta Neurochir (1995) [Suppl] 64, pp. 119-124.
Holsheimer et al., "Spinal Geometry and Paresthesia Coverage in Spinal Cord Stimulation", Neuromodulation, 1998, vol. 1, No. 3, pp. 129-136.
Huff, Terry B. et al., "Real-Time CARS Imaging Reveals a Calpain—Dependent Pathway for Paranodal Myelin Retraction during High-Frequency Stimulation", PLoS ONE, vol. 6, Issue 3 (Mar. 3, 2011): e17176, 11 pgs., doi:10.1371/journal.pone.0017176.
Jeffrey et al., "A reliable method for intracranial electrode implantation and chronic electrical stimulation in the mouse brain", BMC Neuroscience. Biomed Central. London, GB. vol. 14. No. 1, Aug. 6, 2013 (Aug. 6, 2013), pp. 1-8.

(56) References Cited

OTHER PUBLICATIONS

Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi:10.1109/IEMBS. 20113.6091671.

Kent et al., AR, "Recording evoked potentials during deep brain stimulation: development and validation of instrumentation to suppress the stimulus artefact", J Neural Eng., Jun. 2012, vol. 9, No. 3, 036004, doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, Aug. 2003, vol. 50. No. 8, pp. 999-1011.

Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi:10.1016/S0306-4522(98)00022-0.

Kopelman et al., "Attempted Reversible Sympathetic Ganglion Block by an Implantable Neurostimulator", Interactive CardioVascular and Thoracic Surgery, Feb. 7, 2012, vol. 14, Issue 5, pp. 605-609, doi:10.1093/icvts/ivr137.

Krames et al., "Neuromodulation", 1st Edition, Academic Press, 2009, pp. 540-541.

Krarup, Christian, "Compound sensory action potential in normal and pathological human nerves", Muscle & Nerve, Apr. 2004, vol. 29, No. 4, pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Sep. 11, 1999, vol. 53, No. 4, pp. 871-874, doi:10.1212/WNL.53.4.871.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott, "The Electrode-Tissue Interface During Recording and Stimulation in The Central Nervous System", Thesis, 155 pgs., published May 2010.

Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.

Li, S et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Mahnam, A. et al., "Measurement of the Current-Distance Relationship Using a Novel Refractory Interaction Technique", J. Neural Eng. 6, 2009, 22 pgs.

Macefield, "Spontaneous and Evoked Ectopic Discharges Recorded from Single Human Axons", Muscle & Nerve 21, No. 4, Apr. 1998, pp. 461-468.

Markandey, Vishal, "ECG Implementation on the TMS320C5515 DSP Medical Development Kit (MDK)", Texas Instruments Application Report Jun. 2010, 35 pgs.

Matzner et al., "Na+ Conductance and the Threshold for Repetitive Neuronal Firing", Brain Research 597, No. 1 (Nov. 27, 1992): 92-98, doi:10.1016/0006-8993(92)91509-D.

Mcgill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.

Misawa et al., "Neuropathic Pain is Associated with Increased Nodal Persistent Na(+) Currents in Human Diabetic Neuropathy", Journal of the Peripheral Nervous System: JPNS, 14, No. 4 (Dec. 2009): 279-284.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10. 1016/0304-3959(84)90013-7.

Oakley et al., "Spinal Cord Stimulation: Mechanisms of Action", Spine 27, No. 22, Nov. 15, 2002, pp. 2574-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Oh et al., "Long-term hardware-related complications of deep brain stimulation", Neurosurgery, vol. 50, No. 6, Jun. 2002, pp. 1268-1274, discussion pp. 1274-1276.

Olin et al., "Postural Changes in Spinal Cord Stimulation Perceptual Thresholds", Neuromodulation, vol. 1, No. 4, 1998, pp. 171-175.

Opsommer, E. et al., "Determination of Nerve Conduction Velocity of C-fibres in Humans from Thermal Thresholds to Contact Heat (Thermode) and from Evoked Brain Potentials to Radiant Heat ($CO_2$ Laser)", Neurophysiologie Clinique 1999, vol. 29, pp. 411-422.

Orstavik, Kristin et al., "Pathological C-fibres in patients with a chronic painful condition", Brain (2003), 126, 567-578.

Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.

Parker et al., "Compound Action Potentials Recorded in the Human Spinal Cord During Neurostimulation for Pain Relief", Pain, vol. 153, 2012, pp. 593-601.

Parker et al., "Electrically Evoked Compound Action Potentials Recorded From the Sheep Spinal Cord", Neuromodulation, vol. 16, 2013, pp. 295-303.

Penar et al., "Cortical Evoked Potentials Used for Placement of a Laminotomy Lead Array: A Case Report", Neuromodulation: Technology at the Neural Interface, accessed Apr. 19, 2011, doi: 10.1111/j.1525-1403.2011.00352.x.

Rattay, "Analysis of Models for External Stimulation of Axons", IEEE Transactions on Biomedical Engineering, vol. BME-33, No. 10, Oct. 1986, pp. 974-977.

Richter et al., "EMG and SSEP Monitoring During Cervical Spinal Cord Stimulation", Journal of Neurosurgical Review 2011, Southern Academic Press, 1(S1), 2011, pp. 61-63.

Ridder et al., "Burst Spinal Cord Stimulation for Limb and Back Pain", World Neurosurgery, 2013, 9 pgs.

Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.

Roy, S. H. et al., "Effects of Electrode Location on Myoelectric Conduction Velocity and Median Frequency Estimates", J. Appl. Physiol. 61 (4), 1986, pp. 1510-1517.

Sayenko et al., "Neuromodulation of evoked muscle potentials induced by epidural spinal-cord stimulation in paralyzed individu-

(56) References Cited

OTHER PUBLICATIONS als", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating All Parkinsonian Symptoms", Issue: vol. 35(6), Dec. 1994, p. 1126-1130; Copyright: Copyright © by the Congress of Neurological Surgeons; Publication Type: [Technique and Application, ISSN: 0148-396X; Accession: 00006123-199412000-00016; Keywords: Chronic deep brain stimulation, Pallidum, Parkinson's disease, Stereotactic operation.
Siegfried et al., "Intracerebral Electrode Implantation System", Journal of Neurosurgery, vol. 59, No. 2, Aug. 1983, pp. 356-3591.
Srinivasan, S, "Electrode/Electrolyte Interfaces: Structure and Kinetics of Charge Transfer", Fuel Cells, 2006, Chapter 2, 67 Pages.
Struijk, "The Extracellular Potential of a Myelinated Nerve Fiber in an Unbounded Medium and in Nerve Cuff Models", Biophysical Journal vol. 72 Jun. 1997 2457-2469.
Struijk et al., "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.

Mllavicencio, Alan T. "Laminectomy versus Percutaneous Electrode Placement for Spinal Cord Stimulation," Neurosurgery, vol. 46 (2), Feb. 2000, pp. 399-405.
Vleggeert et al., LANKAMP, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in AB Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L., "Pulse Width Programming in Spinal Cord Stimulation: a Clinical Study", Pain Physician. 2010. vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al., "Recording monophasic action potentials using a platinum-electrode ablation catheter", Europace. Oct. 2000; 2(4):312-319.
Communication Pursuant to Article 94(3) EPC, for European Patent Application No. 14861553.7, dated Nov. 4, 2022, 8 Pgs.
Extended European Search Report for European Application 19876581.0 Search Completed Jun. 7, 2022, dated Jun. 15, 2022, 7 pgs.
Extended European Search Report for European Application No. 19875139.8, Search completed Jun. 7, 2022, dated Jun. 15, 2022, 8 Pgs.
Extended European Search Report for European Application No. 19899138.2, Search completed Jul. 26, 2022, dated Aug. 3, 2022, 09 Pgs.
Islam et al., "Methods for artifact detection and removal from scalp EEG: A review", Neurophysiologie Clinique—Clinical Neurophysiology, vol. 46, No. 4, pp. 287-305, XP029804850, ISSN: 0987-7053, DOI: 10.1016/J.NEUCLI.2016.07.002, 2016.
Li et al., "Therapeutic Deep Brain Stimulation in Parkinsonian Rats Directly Influences Motor Cortex", NEURON, vol. 76, No. 5 , pp. 1030-1041, XP0289601 09, ISSN: 0896-6273, 001: 10.1 016/J.NEURON.2012.09.032, 2012.
Shepherd et al., "Electrical stimulation of the auditory nerve: II. Effect of stimulus waveshape on single fibre response properties", Hearing Research, 1999, 130, pp. 171-188.

* cited by examiner

ELECTRODE TO NERVE DISTANCE ESTIMATION

CROSS-REFERENCE TO RELATED APPLICATIONS

This application is a continuation of U.S. Pat. No. 10,894,158, filed Sep. 26, 2017, and granted Jan. 19, 2021, which is national stage of Application No. PCT/AU2016/050263, filed Apr. 8, 2016, which application claims the benefit of Australian Provisional Patent Application No. 2015901270, filed Apr. 9, 2015, the disclosures of which are incorporated herein by reference in their entireties.

TECHNICAL FIELD

The present invention relates to neurostimulation, and in particular relates to observing evoked compound action potentials caused by electrical stimuli, in order to estimate a distance, or a change in distance, between a nerve and an electrode being used to stimulate the nerve.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

For a number of reasons it is desirable to be able to determine the distance of a nerve fibre responding to electrical stimulation from the stimulating electrode. Conventionally, spinal cord stimulation (SCS) delivers stimulation to the dorsal column at a fixed current. When a subject moves or changes posture the distance between the spinal cord and the implanted electrode array varies, resulting in an increase or decrease in the amount of current received by the dorsal columns. These changes in current result in changes to recruitment and paraesthesia, which can reduce the therapeutic effect of SCS and can create side effects including over-stimulation.

If a stimulus is of an amplitude and/or peak width and/or has other parameter settings which put it below the recruitment threshold, delivery of such a stimulus will fail to recruit any neural response. Thus, for effective and comfortable operation, it is necessary to maintain stimuli amplitude or delivered charge above the recruitment threshold. It is also necessary to apply stimuli which are below a comfort threshold, above which uncomfortable or painful percepts arise due to increasing recruitment of $A\delta$ fibres which are thinly myelinated sensory nerve fibres associated with joint position, cold and pressure sensation. In almost all neuromodulation applications, a single class of fibre response is desired, but the stimulus waveforms employed can recruit action potentials on other classes of fibres which cause unwanted side effects, such as muscle contraction if motor fibres are recruited. The task of maintaining appropriate stimulus amplitude is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Another control problem, facing neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of estimating a nerve-to-electrode distance, the method comprising:

applying from a stimulus electrode to a nerve at least one stimulus having defined stimulus parameters;

obtaining a plurality of neural measurements of at least one compound action potential evoked by the at least one stimulus:

processing the plurality of neural measurements in order to estimate an originating state of stimulation, the originating state of stimulation exhibiting at least one observable characteristic defined by a single fibre size; and applying a single fibre model to the estimated originating state of stimulation and the stimulus parameters, in order to produce a measure of the nerve-to-electrode distance.

According to a second aspect the present invention provides an implantable device for estimating a nerve-to-electrode distance, the device comprising:

at least one stimulus electrode and at least one sense electrode;

measurement circuitry for obtaining a neural measurement from the or each sense electrode; and a processor configured to apply from the or each stimulus electrode to a nerve at least one stimulus having defined stimulus parameters, obtain from the measurement circuitry a plurality of neural measurements of at least one compound action potential evoked by the at least one stimulus, process the plurality of neural measurements in order to estimate an originating state of stimulation, the originating state of stimulation exhibiting at least one observable characteristic defined by a single fibre size; and apply a single fibre model to the estimated originating state of stimulation and the stimulus parameters, in order to produce a measure of the nerve-to-electrode distance.

The originating state of stimulation may be considered as a threshold condition of stimulation, at which a single fibre or a single fibre size dominates or defines the nature of the evoked neural response. The present invention recognises that by estimating the originating state of stimulation, it is possible to isolate at least one characteristic which is defined by a single fibre size. Knowledge of an evoked characteristic which is defined solely or largely by a single size of neural fibre in turn enables a single fibre model of recruitment to be applied, in order to estimate the nerve-to-electrode distance. The present invention thus operates to eliminate complicating effects arising from propagation of a compound action potential along a group of neural fibres of distinct size.

Any suitable single fibre model may be applied to the originating state of stimulation in order to produce the measure of nerve-to-electrode distance. The single fibre model may comprise a lookup table matching the observed characteristic and the stimulus parameters to a corresponding nerve-to-electrode distance.

The measure of the nerve-to electrode distance may comprise an absolute measure of distance, or a relative measure reflecting a change in distance from a previous time, or a measure of a rate of change of distance.

In some embodiments of the invention, the method may comprise the further step of adjusting a therapeutic stimulus regime in response to an observed change in the nerve-to-electrode distance.

In some embodiments of the invention, the method may be performed intra-operatively, as part of a surgical procedure, for example to progressively monitor a position of a structure bearing the electrodes relative to the nerve. In some embodiments the method may be conducted as part of a postoperative fitting procedure of a neurostimulator.

In some embodiments of the invention the originating state of stimulation may comprise an estimate of the ECAP peak width at the stimulus site. In such embodiments the applying comprises applying a single stimulus in order to evoke a single ECAP, and the plurality of neural measurements are obtained from at least two sense electrodes each at a unique distance away from the stimulus electrode. Such embodiments recognise that an ECAP comprises a compound response made up of contemporaneous action potentials evoked on a plurality of individual nerve fibres, and that each nerve fibre exhibits a conduction velocity which depends at least partly on the diameter of that fibre, so that the ECAP peak width widens at an approximately linear rate as each individual action potential propagates away from the stimulus site at a unique velocity. Such embodiments preferably estimate an originating ECAP peak width by extrapolating the first and second ECAP measures back to the stimulus site, given that a distance from the stimulus electrode to the first and second sense electrodes is known. Such embodiments of the invention recognise that the originating ECAP peak width can be assumed to be dominated by that single fibre recruited at the stimulus site which had the broadest action potential peak width, typically comprising the recruited fibre of largest diameter as larger fibers are more excitable than smaller diameter fibers. Such embodiments further recognise that the nerve-to-electrode distance can in turn be estimated from the originating ECAP peak width because of the dependence of originating ECAP dispersion upon the fibre to electrode distance.

Such embodiments, which estimate the originating ECAP peak width or dispersion, may be particularly suitable in applications where the stimulus and sense electrodes are well aligned alongside a neural pathway, such as in the case of SCS.

The measure of ECAP peak width may comprise a half-height peak width, being a measure of a width of an ECAP peak as observed at an amplitude which is half the amplitude of the peak amplitude of the observed ECAP peak. Alternatively the measure of ECAP peak width may comprise a time between the N1 and P peaks of the observed response, and/or a time between the P1 and P2 peaks. Alternatively the measure of ECAP peak width may comprise a time between a zero crossing preceding the N1 peak and a zero crossing following the N1 peak.

The ECAP peak width may be measured or assessed by extracting frequency components of the neural measurements, for instance fast Fourier transform. Preferably the neural measurements are first windowed to exclude discontinuities or like stimulus effects and/or measurement effects. The frequency domain information of the respective neural measurements may then be used to extract a measure of the dispersion. For example a profile of the frequency domain spectrum of the neural measurements may be assessed for a roll-off or decay with frequency, whereby a faster roll-off of higher frequency components reflects a more dispersed ECAP peak, that is, a peak which is more dominated by lower frequency components. A slope or rate of decay of the frequency roll-off may then be determined for each neural measurement, and used to estimate an originating state of stimulation namely the frequency roll-off present in the evoked response at the site of stimulation. Such embodiments may be advantageous in measuring dispersion in noisy neural measurements, as a frequency roll-off can be averaged or fitted over a relatively wide spectral range. Such embodiments may further be advantageous in enabling a measure of dispersion to be obtained without reliance on the amplitude of the ECAP, for example in embodiments where manual user feedback or automated feedback operates to control recruitment at a substantially constant level.

The measure of ECAP peak width may comprise a function of one or more such measures, or may comprise any measure which reflects dispersion of the ECAP over time.

In some embodiments, neural measurements may be obtained of both orthodromic and antidromic ECAPs, to permit an averaged or more robust estimate of the originating state of stimulation, and thus of the nerve-to-electrode distance estimate, to be obtained.

Additionally or alternatively, the originating state of stimulation may in some embodiments comprise a stimulus threshold such as the Rheobase. In such embodiments, a stimulus threshold is preferably determined at at least two differing stimulus pulse widths, from which the Rheobase can be calculated. The conduction velocity is preferably measured and used to determine a fibre diameter recruited at threshold. Fitted relationships of the modelled single fibre Rheobase to the electrode-to-nerve separation are then used to determine the separation. Such embodiments may be particularly advantageous in applications providing or permitting only one measurement electrode, as may occur in the brain which does not comprise a single longitudinal neural pathway.

The originating state of stimulation may in some embodiments be selectively explored in relation to a sub-population of fibres as defined by refractory period. Such embodiments recognise that the fibres within the population of recruited fibres may have different refractory periods. The originating state of stimulation may be estimated in relation to a specific sub-population of the fibres selected for different refractory periods, for example by applying a stimulus sequence comprising a first stimulus referred to as a masker stimulus which recruits all the fibres of interest, and then a short duration later applying a second stimulus referred to as a probe stimulus. The duration between the masker and probe stimuli is selected to be longer than the refractory period of some fibres, but shorter than the refractory period of other fibres. Consequently, the probe stimulus will recruit only those fibres having a short enough refractory period to have recovered from the masker stimuli and able to be recruited a second time by the probe stimulus. In such embodiments the neural measurements are then analysed specifically in relation to the portion of the observed measurement which corresponds with the response evoked by the probe stimulus.

Embodiments of the invention may thus be applied in neural stimulation applications where the separation between the responding fibres and the stimulating electrode varies often or even continuously with patient movement, whereby knowledge of the fibre-to-electrode distance or at least of incremental changes thereof, would be valuable. Other embodiments of the invention may be applied in relation to locating responding fibres three dimensionally in space in order to avoid or locate them during a surgical or imaging procedure for example. In another application it is desirable to be able to locate a target fibre and position an electrode array in optimal position relative to the fibre in order to achieve the most effective stimulation. Such embodiments may further comprise identifying a target nerve fascicle within a larger nerve bundle, at differing locations along the nerve bundle, in order to detect variation in position of the fascicle within the bundle.

In some embodiments, the ECAP measurements are further used to estimate the distribution of fiber diameters present in an ECAP. An indication of the distribution or spread of fiber diameters can provide a useful validation for computer models and may be used to inform device and algorithm design to improve outcomes for SCS.

Thus, according to a third aspect, the present invention provides a method of estimating a distribution of fibres recruited by a stimulus, the method comprising obtaining from at least two sense electrodes spaced apart along a neural pathway respective measurements of a compound action potential propagating along the neural pathway:

determining a conduction velocity of the compound action potential from the latency between the measurements, and determining from the conduction velocity a dominant recruited fibre diameter;

determining a rate of dispersion of the compound action potential between the sense electrodes, and determining from the rate of dispersion a distribution of diameters of the recruited fibre population.

According to a fourth aspect, the present invention provides a device for estimating a distribution of fibres recruited by a stimulus, the device comprising at least one stimulus electrode and at least two sense electrodes, configured to be spaced apart along a neural pathway:

measurement circuitry for obtaining a neural measurement from each sense electrode; and a processor configured to obtain from the at least two sense electrodes respective measurements of a compound action potential propagating along the neural pathway, determine a conduction velocity of the compound action potential from the latency between the measurements, determine from the conduction velocity a dominant recruited fibre diameter, determine a rate of dispersion of the compound action potential between the sense electrodes, and determine from the rate of dispersion a distribution of diameters of the recruited fibre population.

In embodiments of the third and fourth aspects of the invention, the rate of dispersion may be determined in any suitable manner described herein, including any one or more of the observed ECAP peak width, ECAP peak spacing. ECAP zero crossings, ECAP half-height peak width or ECAP spectral content.

The third and fourth aspects of the invention recognize that the overall distribution of fibre diameters, the distribution of fibre diameters recruited by a given stimulus, and/or the recruited fibres' conduction velocities may vary from one subject to the next. Moreover, some embodiments further recognize that variations in such characteristics may be correlated with the neurological condition which brought about the need for neurostimulation: for example, changes in conduction velocity and distribution of fibre diameters in dorsal columns have been recorded in mouse models of neuropathic pain as a result of central sensitization. Some embodiments of the third and fourth aspects of the present invention may thus further comprise treating the neurological condition by administering or modifying a therapy in a manner responsive to the determined distribution of diameters of the recruited fibre population, or responsive to a change in the determined distribution over time.

According to a further aspect the present invention provides a non-transitory computer readable medium for estimating a nerve-to-electrode distance, comprising instructions which, when executed by one or more processors, causes performance of the following:

applying from a stimulus electrode to a nerve at least one stimulus having defined stimulus parameters;

obtaining a plurality of neural measurements of at least one compound action potential evoked by the at least one stimulus;

processing the plurality of neural measurements in order to estimate an originating state of stimulation, the originating state of stimulation exhibiting at least one observable characteristic defined by a single fibre size; and applying a single fibre model to the estimated originating state of stimulation and the stimulus parameters, in order to produce a measure of the nerve-to-electrode distance.

According to a further aspect the present invention provides a non-transitory computer readable medium for estimating a distribution of fibres recruited by a stimulus, comprising instructions which, when executed by one or more processors, causes performance of the following:

obtaining from at least two sense electrodes spaced apart along a neural pathway respective measurements of a compound action potential propagating along the neural pathway;

determining a conduction velocity of the compound action potential from the latency between the measurements, and determining from the conduction velocity a dominant recruited fibre diameter;

determining a rate of dispersion of the compound action potential between the sense electrodes, and determining from the rate of dispersion a distribution of diameters of the recruited fibre population.

BRIEF DESCRIPTION OF THE DRAWINGS

An example of the invention will now be described with reference to the accompanying drawings, in which.

DESCRIPTION OF THE PREFERRED EMBODIMENTS

Figure 1:
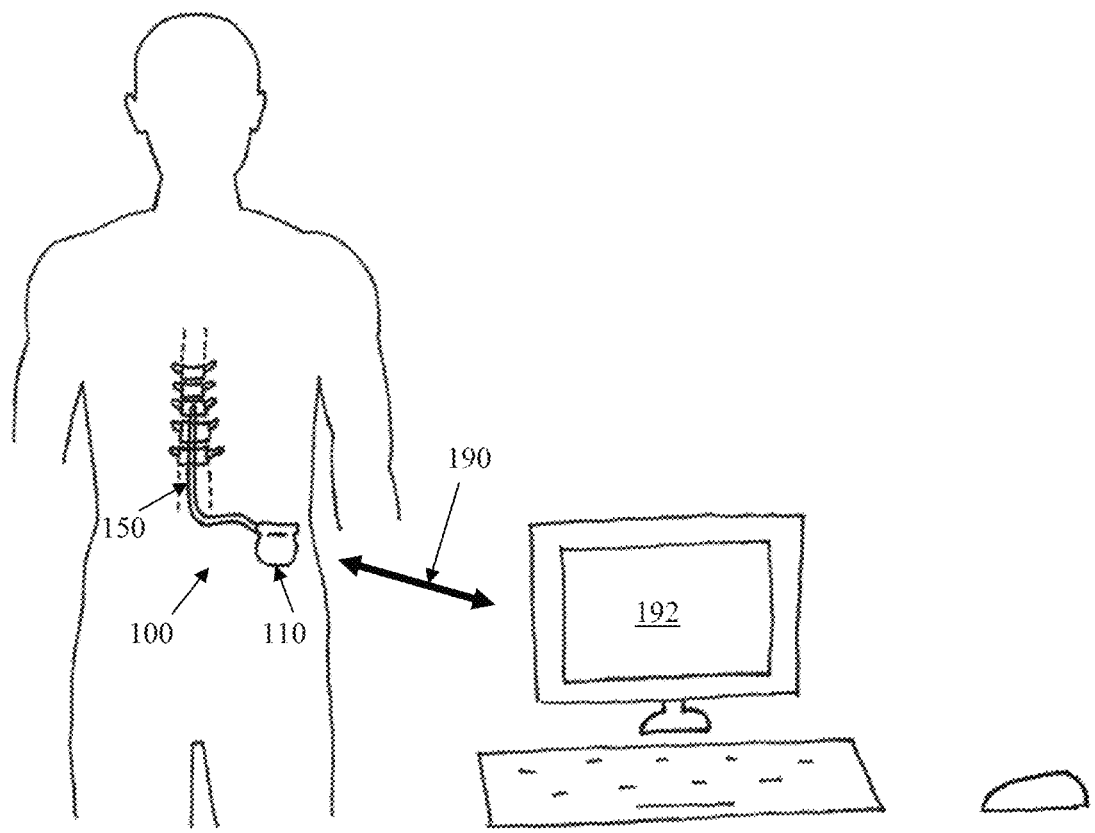
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 2:
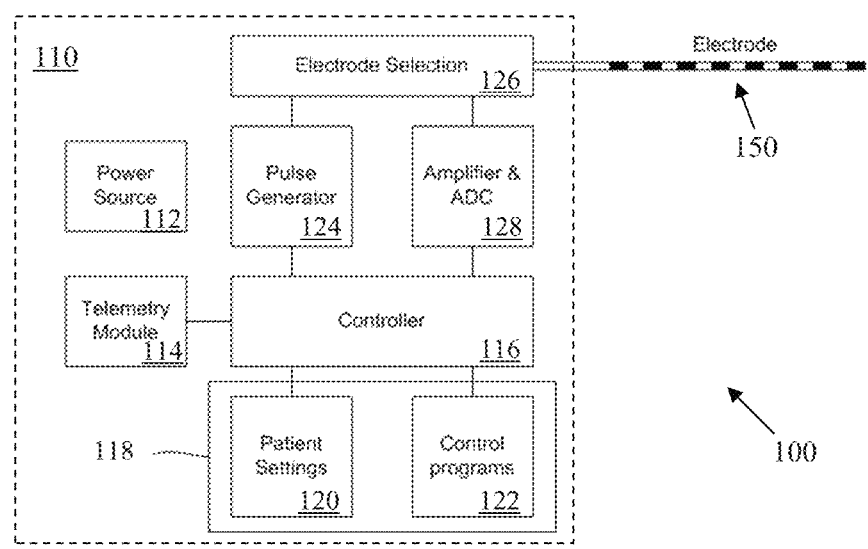
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

Figure 3:
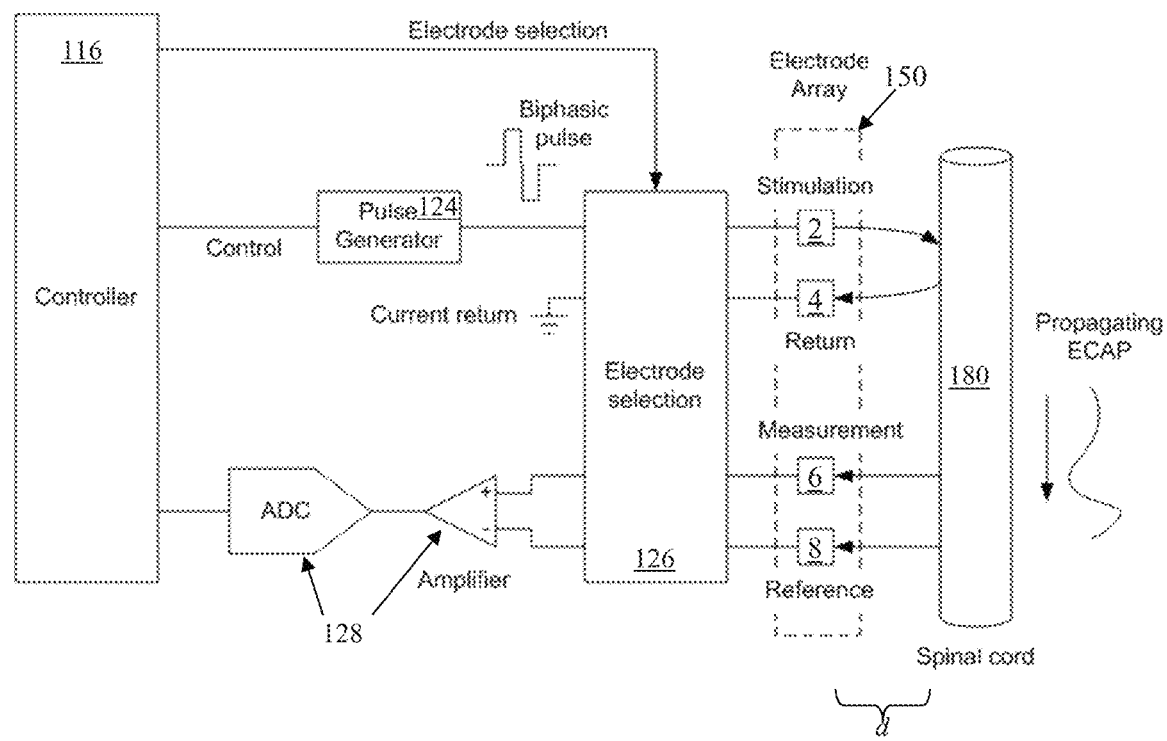
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at 30 Hz. To fit the device, a clinician applies stimuli which produce a sensation that is experienced by the user as a paraesthesia. When the paraesthesia is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

The present invention recognises that the amplitude and morphology of an ECAP measurement depends on a number of factors, including the quantity of recruited fibres contributing to the compound response, the conduction velocity or diameter of each recruited fibre, the separation of the electrode from the fibres in both the radial direction and the axial direction relative to an axis of the fibre, and the separation of the measurement electrode(s) from the stimulus electrode(s).

Here we present methods to determine the separation of fibres from stimulation electrodes based on measurement of ECAPs. There are a number of techniques which can be used to eliminate variables in order to isolate the nerve-to-electrode distanced.

A first such technique is to estimate characteristics of the ECAP response as it existed when first evoked directly under or adjacent to the stimulation electrode 2. In this way, the effect of propagation of the response can be eliminated, allowing an estimation of the separation from the threshold current and conduction velocity of the fibre. Thus, the present embodiment of the invention recognises that the ECAP response as it first existed directly adjacent the stimulus electrode 2 is one type of an originating state of stimulation which can be useful in estimating d.

Figure 4:
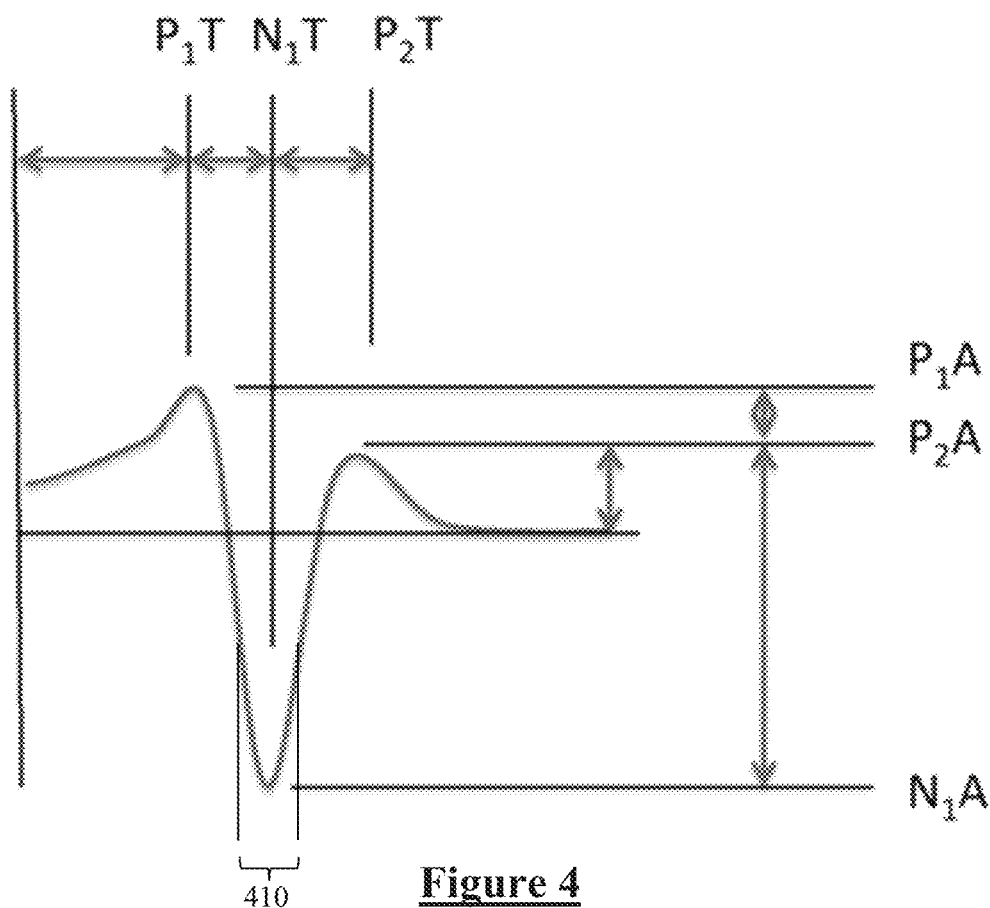
FIG. 4 illustrates the typical form of an electrically evoked compound action potential (ECAP) of a healthy subject.

FIG. 4 illustrates the typical form of an electrically evoked compound action potential (ECAP) of a healthy subject. The shape of the compound action potential shown in FIG. 4 is predictable because it is a result of the ion currents produced by the ensemble of axons generating action potentials in response to stimulation. The action potentials generated among a large number of fibres sum to form a compound action potential (CAP). The CAP is the sum of responses from a large number of single fibre action potentials. The CAP recorded is the result of a large number of different fibres depolarising. The propagation velocity of the action potential on each fibre is determined largely by the diameter of that fibre. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts.

The CAP profile takes a typical form and can be characterised by any suitable parameter(s) of which some are indicated in FIG. 4. Depending on the polarity of recording, a normal recorded profile may take an inverse form to that shown in FIG. 4, i.e. having two negative peaks N1 and N2, and one positive peak P1.

Figure 5:
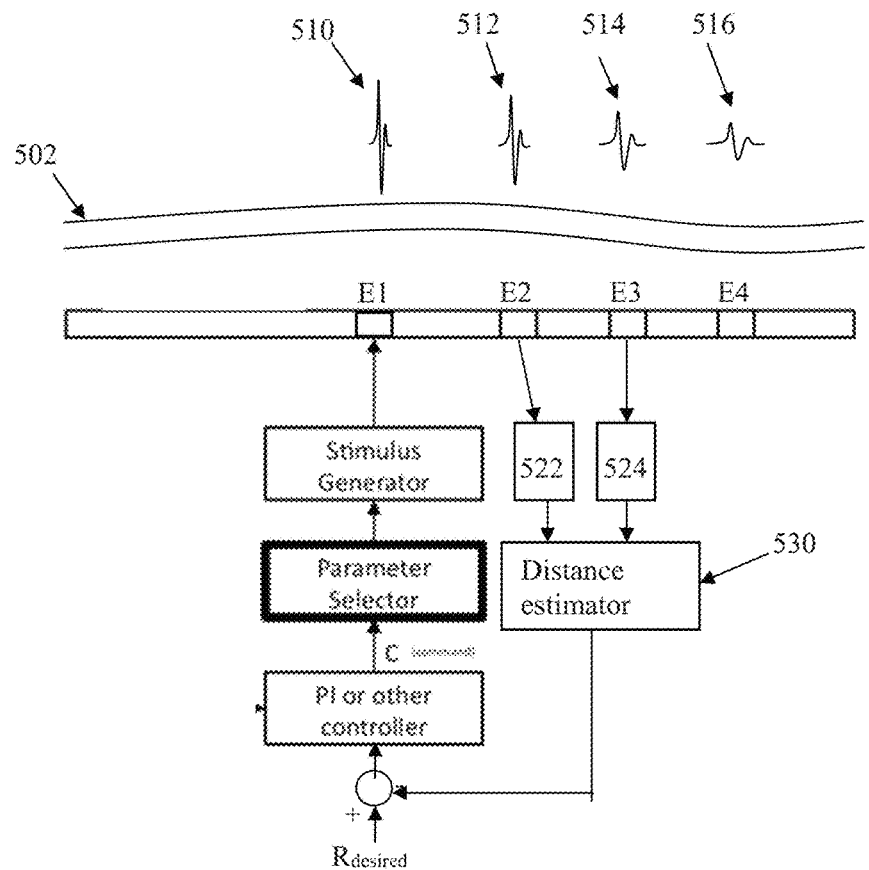
FIG. 5 illustrates stimulus of a nerve and dispersion and measurement of a response.

In this embodiment, electrical stimuli are delivered to the spinal cord 502 by one or more stimulus electrodes denoted E1 in FIG. 5. A desired degree of recruitment, $R_{desired}$, is input by the user or by a setting made by a clinician when fitting the device or by any other suitable means for defining desired recruitment. $R_{desired}$ is processed by a controller and selector and passed to a stimulus generator which generates a stimulus to be delivered to the neural tissue by electrode E1. As will be appreciated, while only a single stimulus electrode E1 is shown in FIG. 5, a bipolar, monopolar or tripolar stimulus may be applied in conjunction with other stimulus electrodes, not shown. At the stimulus site adjacent to E1 within the spinal cord 202, a neural response 510 is evoked by the stimulus.

The neural response evoked by the stimulus at E1 is a compound response comprising the individual responses evoked in a number of fibres, and takes a form shown at 510. The evoked response 510 propagates along the recruited fibres within the spinal cord 502 away from the stimulus site adjacent to E1, and in so doing the form or morphology of the compound response alters or decays. Without intending to be limited by theory, the decay in the neural response as it travels is at least in part due to a spreading of the compound response along the spinal cord 502 resulting from each recruited fibre having a conduction velocity which differs from the conduction velocity of other recruited fibres. The alteration or decay in the morphology of the observed neural response as it travels is also in part due to a spreading of the compound response across the cross section of the spinal cord 502 due to the variation in depth of the recruited fibres within the cord 502 at different positions along the cord. At a time t2 the compound response passes sense electrode E2 and is recorded as having an amplitude and duration indicated at 512, which differs from the form of the response at 510 in that response 512 is of reduced amplitude and greater width or duration. At a later time $t_3$, after undergoing further spreading and decay, the compound response passes sense electrode E3 and is recorded as having an amplitude and duration indicated at 514. Observed response 514 is of lesser amplitude but greater duration then observed response 512. Similarly, at a later time $t_4$, after undergoing further spreading and decay, the compound response passes electrode E4 and is recorded as having a further decreased amplitude and increased duration as indicated at 516. Observed response 516 is of lesser amplitude but greater duration then observed response 514.

It is to be appreciated that the form of each observed response, as shown at 510, 512, 514 and 516, is illustrative. The decay and spreading observed in any neural response will depend at least upon the characteristics of the fibre population actually recruited by the stimulus, the neurophysiology of the subject, and the distance of the electrodes from the fibres.

In accordance with the present invention, electrodes E2 and E3 are used to obtain a first measurement 512 and a second measurement 514 of the neural response evoked by the stimulus, via measurement circuitry 522, 524 respectively. The evoked CAP measurements in this embodiment are made by use of the neural response measurement techniques set out in International Patent Publication No. WO2012/155183, with two data channels recording simultaneous data from the two electrodes E2 and E3.

An improved knowledge of the electrophysiological response may lead to explanations of the large variability which is observed in outcomes from SCS and may provide valuable insight into electrode and device design, and improved stimulation algorithms.

Without intending to be limited by theory, it is noted that the total potential electric field external to and produced from a single nerve fibre, including fast Na, persistent Na and slow potassium channels and myelin properties, can be modelled by:

$$\varphi(x, h, t) = \frac{\rho}{4\pi} \sum_{n=0}^{\infty} \frac{I_m\left(t - \frac{x_n - x_0}{v}\right)}{\sqrt{h^2 + (x - x_n)^2}}$$

where h is the distance of the measurement electrode from the fibre $x_n$ is the x co-ordinate of each node of Ranvier $I_m$ is the current produced by each node t is time v is the conduction velocity of the fibre.

For very small h, the field amplitude is inversely proportional to h, as the field is dominated by a single node of Ranvier. As the electrode is moved away the amplitude decreases and the relationship changes to a power law as the measurement electrode is influenced by the fields produced by more nodes. The shape of the action potential also changes with distance to the measuring electrode. The action current $I_m$ is weighted and summed at the measurement electrode, but with different delays for each of the nodes $x_n$. The weights change because of the increase in distance from the node to the electrode. This looks like a filter (I/r).

Figure 6:
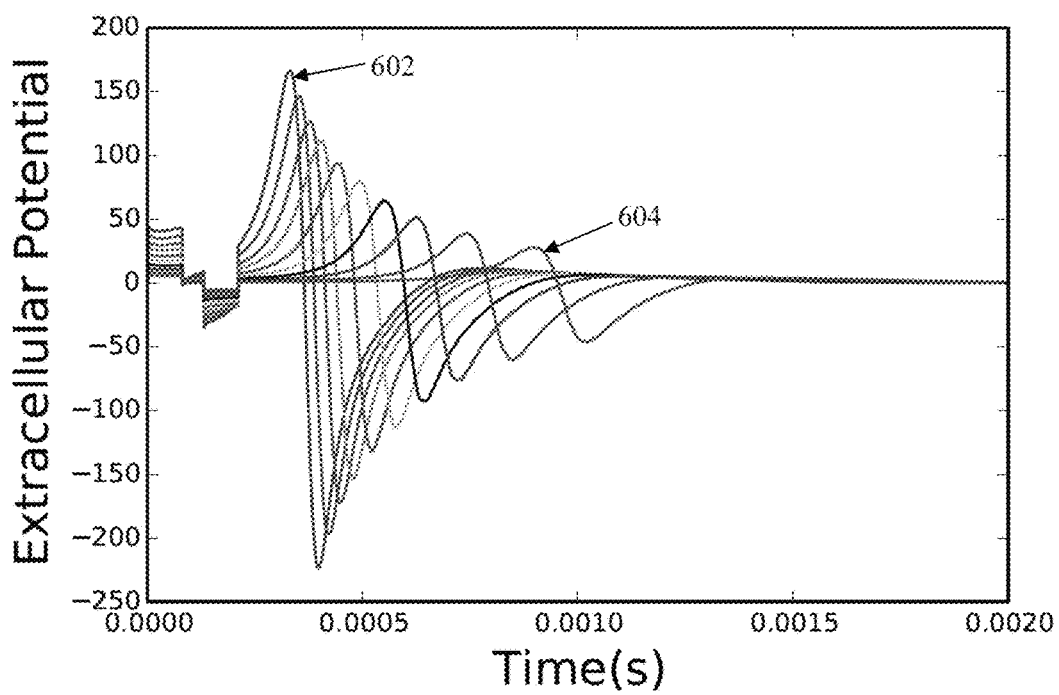
FIG. 6 is a plot of computed single fibre action potentials, for 10 different fibre diameters.

Several suitable models exist for assessing single fibre behaviour, such as models based on Hodgkin Huxley cable models, and any such single fibre model may be used in embodiments of the present invention. With suitably chosen parameters for the ion channel gating functions, FIG. 6 is a plot of computed single fibre action potentials, for 10 different fibre diameters from 19 μm to 8.7 μm. Specifically, plot 602 shows the computed single fibre action potential for a 19 μm diameter fibre, and plot 604 shows the computed single fibre action potential for a 8.7 μm diameter fibre. The large diameter fibres conduct at the highest velocity and the smaller diameter fibres have progressively longer latency and are progressively smaller in size. To calculate a compound action potential requires an estimate of the number of fibres for each size of fibre. The compound action potential is then simply the sum of contributions from all those fibres. That is, the ECAP consists of the contributions of the electrical activity from all the recruited fibers, where the response from a single fiber is referred to as the single fiber action potential (SFAP).

Figure 7:
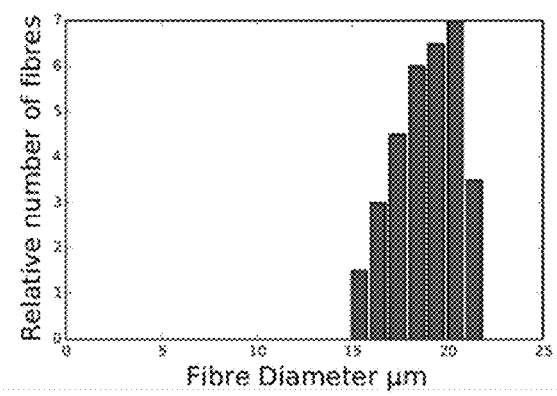
FIG. 7 illustrates a size distribution of a recruited fibre population.

Calculations were made with the modelled measurement electrode positioned from 35 mm to 84 mm away from the stimulation electrode along the neural pathway, at increments of 7 mm. Both the measurement and sense electrodes are modelled as being located directly above, and separated by a nominated distance (h) from, the modelled fibre. A population distribution was generated as a function of fibre diameter, as shown in FIG. 7, in which the Y axis is an arbitrary scale plotted against the diameter of the fibre. The population distribution of FIG. 7 comprises fibres as small as 15 μm, up to 21 μm, in the relative proportions shown.

Figure 8:
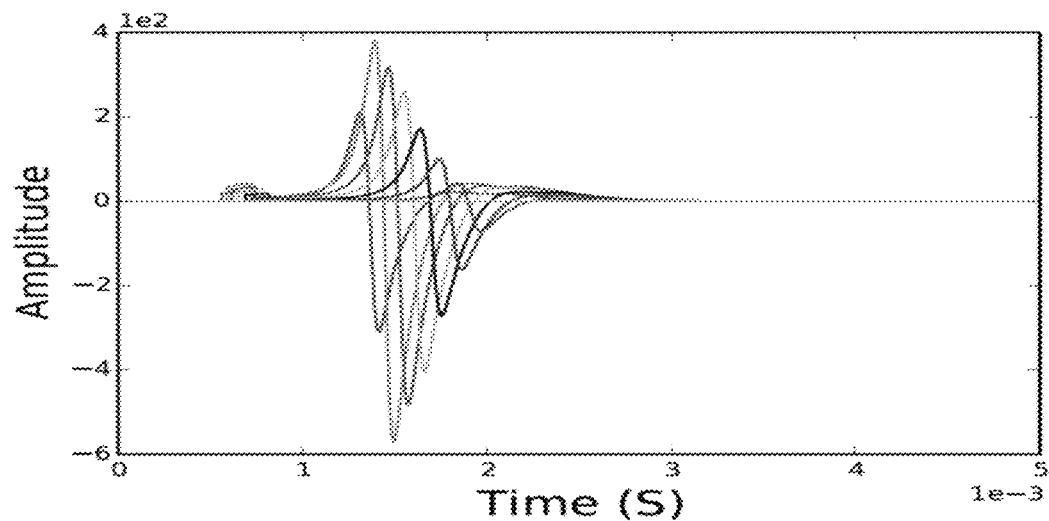
FIG. 8 is a plot of modelled single fibre action potentials, scaled in amplitude according to the distribution of FIG. 7.
Figure 9:
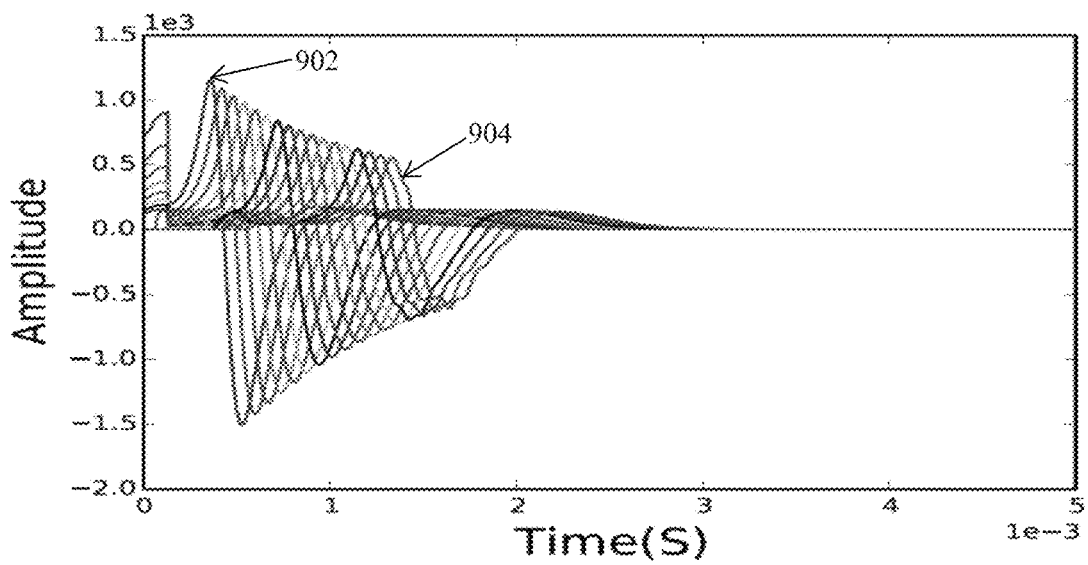
FIG. 9 illustrates the synthetic compound action potential produced by summation of the scaled potentials of FIG. 8, at various distances away from the stimulus location.

FIG. 8 is a plot of each of the single fibre potentials, scaled by the population distribution of FIG. 7 for the modelled fibre diameters, at a single location. The electrode-to-nerve distance was modelled as 6 mm, and FIG. 9 illustrates the synthetic compound action potential calculated at multiple electrode locations by summation of the single fibre responses at each electrode location such as those shown in FIG. 8 for a single location. In particular, FIG. 9 shows such a synthetic compound action potential as observed at each of the electrodes positioned along the nerve and 6 mm away from the nerve, and at a distance of 35 mm to 84 mm away from the stimulus site, respectively. Specifically, plot 902 shows the computed compound action potential as observed at the electrode 35 mm away from the stimulus site, and plot 904 shows the computed compound action potential as observed at the electrode 84 mm away from the stimulus site, with interposed plots shown for respective interposed electrodes. As can be seen in FIG. 9, the simulated compound action potential decays (reduces in amplitude) and disperses (widens) as it travels away from the stimulus site.

A convenient measure of the dispersion of the ECAP is to measure width of the N1 peak at half height, as indicated at 410 in FIG. 4. The observed dispersion is related to the separation of the measurement electrode from the fibre, whereby for a given single action potential or compound action potential a narrower dispersion is observed at a smaller electrode-to-fibre separation and a wider dispersion is observed at a larger separation. This is a result of the previously discussed effect that the closer the electrode is to the fibre, the more the signal observed by the sense electrode is dominated by the nodes of Ranvier that are closest to the electrode. As the electrode-to-fibre distance increases, the signal present at the sense electrode becomes influenced by more nodes of Ranvier positioned along the fibre, dispersing the observed response. This effect sums over many fibres and thus also occurs when measuring contributions from many fibres as is the case in ECAP measurement. However the observed dispersion also depends on the contribution from fibres of different diameter, which each conduct at different velocities. The present embodiment recognises that the relative influence of the fibre population distribution, on one hand, and the relative influence of the height above the cord, on the other hand, can be separated.

Figure 10:
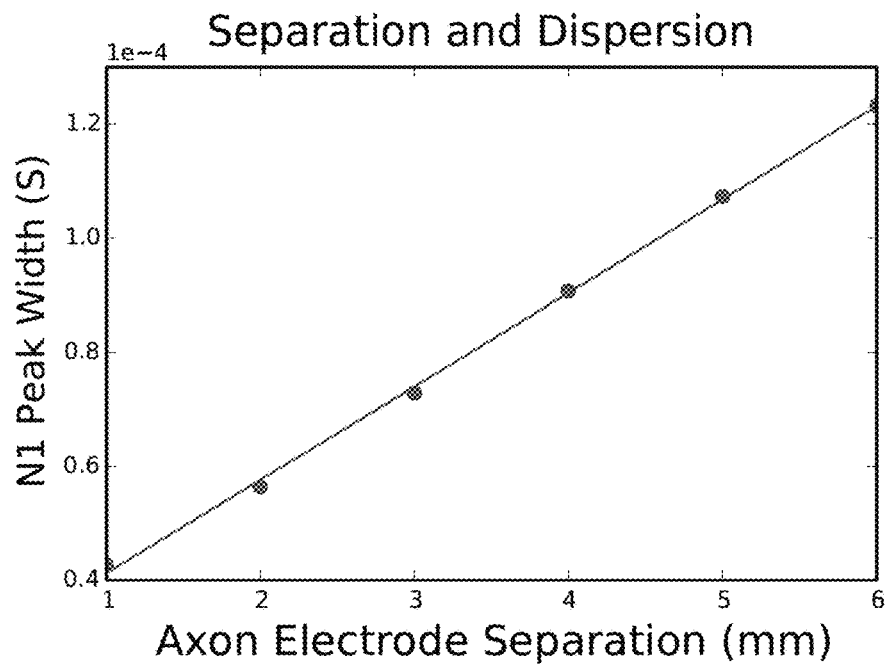
FIG. 10 illustrates the calculated dispersion for a single fibre for a number of differing electrode-to-fibre separations.
Figure 11:
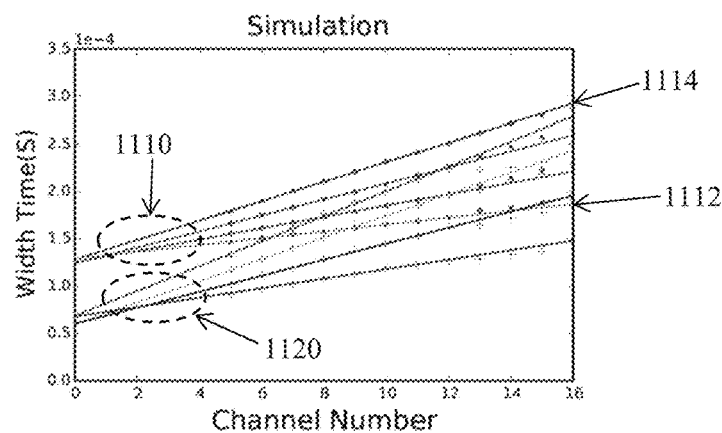
FIG. 11 illustrates the width at half height of the synthetic ECAPs as observed at increasing distance from the stimulus site.

FIG. 10 illustrates the calculated dispersion for a single fibre, being the width 410 of the N1 peak at half height, for a number of differing electrode-to-fibre separations. The relationship is linear and varies by a factor of 4 over the range of separations calculated. However in practice recruitment of a single fibre by device 100 is impossible and the contribution of multiple recruited fibres, of varying diameter, must be taken into account for any practical observations. To this end, synthetic ECAPS were generated for a number of differing fibre populations, for two cases: measurement electrodes positioned at 3 mm above the axon, and at 6 mm above the axon. FIG. 11 illustrates the width at half height of the resulting synthetic ECAPs as observed at channels (electrodes) 5 through 16 at increasing distance from the stimulus site.

As can be seen in FIG. 11, the plot of dispersion of the ECAP varies considerably with changes in the recruited fibre population, even for unchanged electrode-to-nerve separation. For synthetic observations 1110, which all relate to an electrode-to-nerve separation of 6 mm, the variation in recruited fibre population can give dispersion as little as 50 μs between channel 5 and 16 in the case of observation 1112, or as large as 100 μs between channel 5 and 16 in the case of observation 1114. The modelled fibre population distributions at each height comprise a distribution width of 6, 7, 8 or 9 μm, whereby a distribution with an increased number of smaller fibres, and having fibres of a smaller diameter, gives rise to an increased slope of the width at half height of the N1 peak in relation to the propagation distance. Similar variation can be seen in the synthetic observations 1120, which all relate to an electrode-to-nerve separation of 3 mm, for the same four selected fibre distributions.

FIG. 11 shows that the width at half depth of the N1 peak, and thus the CAP dispersion, has a linear dependence on the propagation distance, increasing with propagation distance due to impact of the smaller diameter fibres travelling at slower speeds and increasing the width or dispersion of the peak.

Figure 12:
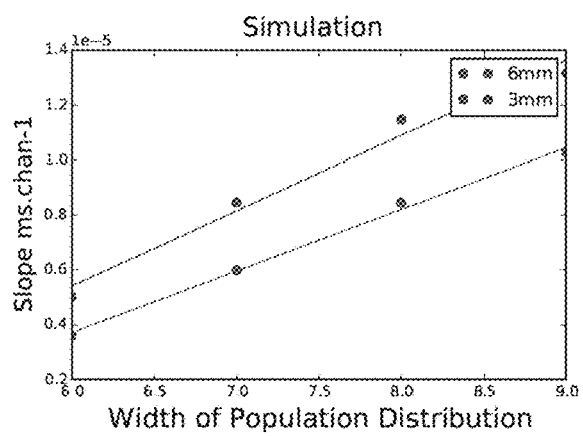
FIG. 12 is a plot of the slope of peak widths relative to four selected population distributions.

FIG. 12 is a plot of the slope, in ms per channel, of the peak widths relative to the four selected population distributions from the same data as FIG. 11. As can be seen, as the population distributions are widened by the addition of smaller fibres, the resulting dispersion increases.

Thus dispersion alone cannot be used to determine electrode to nerve separation because the recruited fibre population's size distribution is an unknown. However, referring again to FIG. 11, the present embodiment recognises that a line or curve fitted to the observed ECAP peak widths and extrapolated to the stimulus site (channel "0" in FIG. 11), gives a value which is substantially independent of the propagation dispersion effects. In particular, all of the curves 1110 meet the y-axis of FIG. 11 at substantially a first point around 125 μs, while all of the curves 1120 meet the y-axis at substantially a second point around 60 μs. Accordingly, in this embodiment the intercept of the lines 1102 or 1104 with the y-axis at channel "0" is taken as the originating state of stimulation. Importantly, propagation dispersion is effectively eliminated by determining the y-intercept. The present embodiment recognises that the y-intercept value of the lines varies with electrode-to-nerve separation. Moreover, the y-intercept can be obtained in practice as simply as by applying one stimulus and obtaining as little as two measurements of the ECAP at spaced-apart sense electrodes, as a line can be fitted to two such data points to estimate a y-intercept. Other embodiments may obtain many sense electrode measurements of a single ECAP in order to improve accuracy, or may determine the y-intercept by any suitable means.

It is further to be noted that the y-intercept value of the lines 1110 and 1120 is impossible to measure directly in practice, as the stimulus applied at the stimulus site is many orders of magnitude larger than the response evoked.

Accordingly, in some embodiments changes in the y-intercept may be used to indicate relative changes in the electrode-to-nerve distance d, even if the absolute value of d is not known.

However, other embodiments further provide for an estimation of the absolute value of the distanced, as follows. These embodiments are based on the recognition that the ECAP peak width at Channel 0 (being the stimulus location) is dominated by the width of the single fibre action potential of the largest recruited fibre contributing to the response. For a given nerve, the largest recruited fibre is typically the most easily recruited and can thus be assumed to have been recruited if any ECAP at all is evoked. The action potential peak width of the largest recruited fibre is a constant, but will be observed as a broader peak with increasing fibre to electrode distance d. Thus, the peak width of the observed response at channel 0 is dependent on the separation d but is substantially independent of the population distribution of the fibres recruited, at least for the range of populations simulated in FIG. 11.

Figure 13:
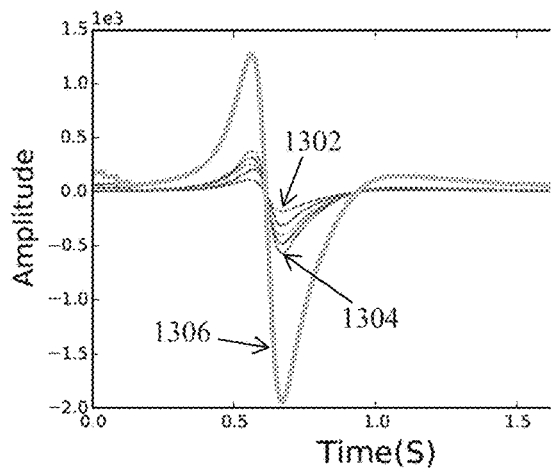
FIG. 13 illustrates single fibre responses as superimposed at the stimulus site

FIG. 13 shows the action potentials calculated for individual fibres over a range of fibre diameters from 18 micron (SFAP 1302) to 23 micron (SFAP 1304), with intervening fibres' action potentials shown but not labelled. The sum of the SFAPs produces the larger CAP 1306. As shown in FIG. 13, the larger diameter fibres produce the largest SFAP responses. When mapped to the stimulus site, the smaller diameter fibres at Channel 0 contribute responses to the compound response 1306 which are enveloped by, or do not significantly affect some key characteristics of, the single fibre response 1304 of the largest contributing fibre diameter.

Figure 14:
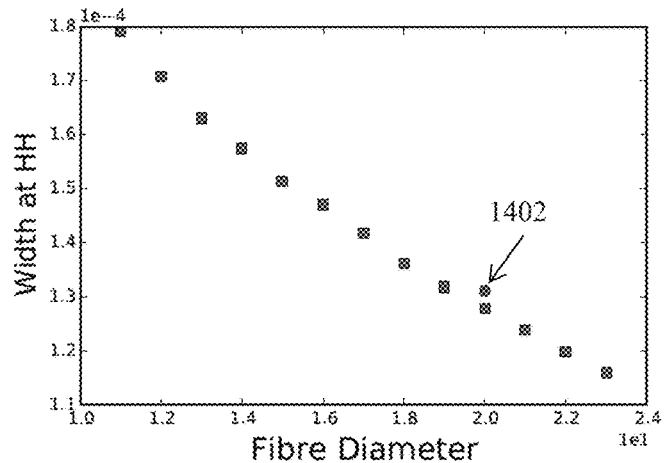
FIG. 14 is a plot of the action potential peak width for single fibres of varying diameters.

FIG. 14 is a plot of the single fibre action potential peak width, for single fibres of varying diameters in the range 11-23 μm, as indicated by square data points. The circular data point 1402 indicates the synthetic compound action potential peak width occurring at channel 0 for the population of fibres shown in FIG. 7. As can be seen from 1402, the 20 μm fibre was the most abundant in this population distribution and the peak width of the ECAP at 1402 was $1.3 \times 10^{-4}$ s whereas the width of a single 20 μm fibre response was $1.27 \times 10^4$ s, which is a 2% error in the approximation. The error gets worse with wider distributions of fibre diameters in the fibre population. With a range of fibres from 14 μm to 23 μm in diameter the width at half depth is 4% larger than the value for the SFAP. The net effect is that the present technique will slightly overestimate the separation of electrode from the responding fibre when the relation evident in FIG. 14 is used to calculate the corresponding distance.

Figure 15A:
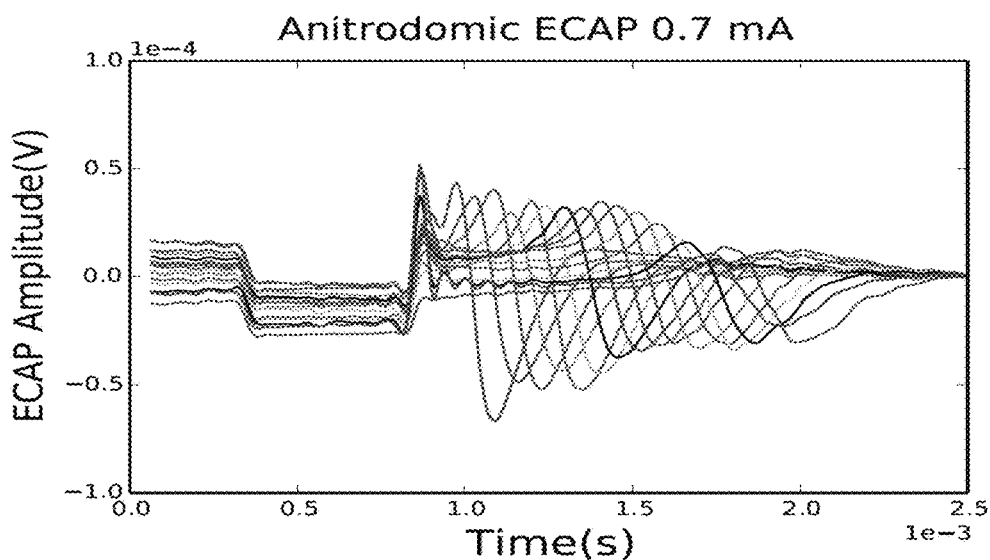
FIG. 15a is an overlaid plot of experimentally obtained measurements of a sheep ECAP obtained from spaced apart measurement electrodes.
Figure 15B:
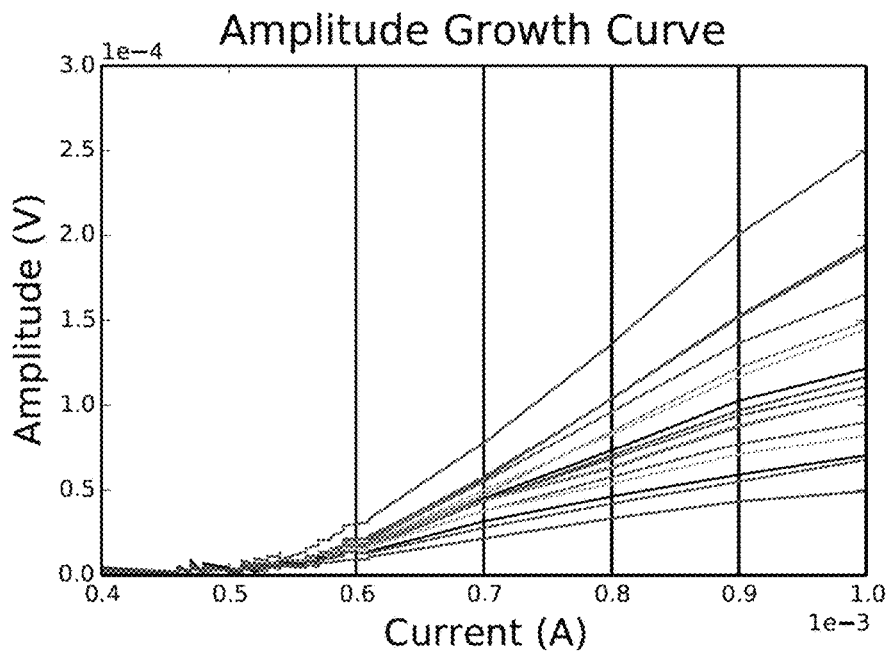
FIG. 15b is a plot of the peak to peak amplitude observed on each such measurement electrode in response to increasing stimulation.

To verify the above theoretical approach, animal (sheep) experiments were conducted by epidural implantation of a 24 channel linear electrode array with electrode spacing of 7 mm. Current sources were configured to produce tripolar stimulation with a central cathode (channel 2) and anodes on each side (channels 1 & 3). Evoked responses were recorded on electrodes 4 to 24. FIG. 15*a* is an overlay of all of the recordings from channels 4 to 24 in response to stimulation at 0.7 mA. FIG. 15*b* is a plot of the peak to peak amplitude observed on each electrode 4 to 24 in response to increasing stimulation from 0.4 mA to 1.0 mA.

Figure 16A:
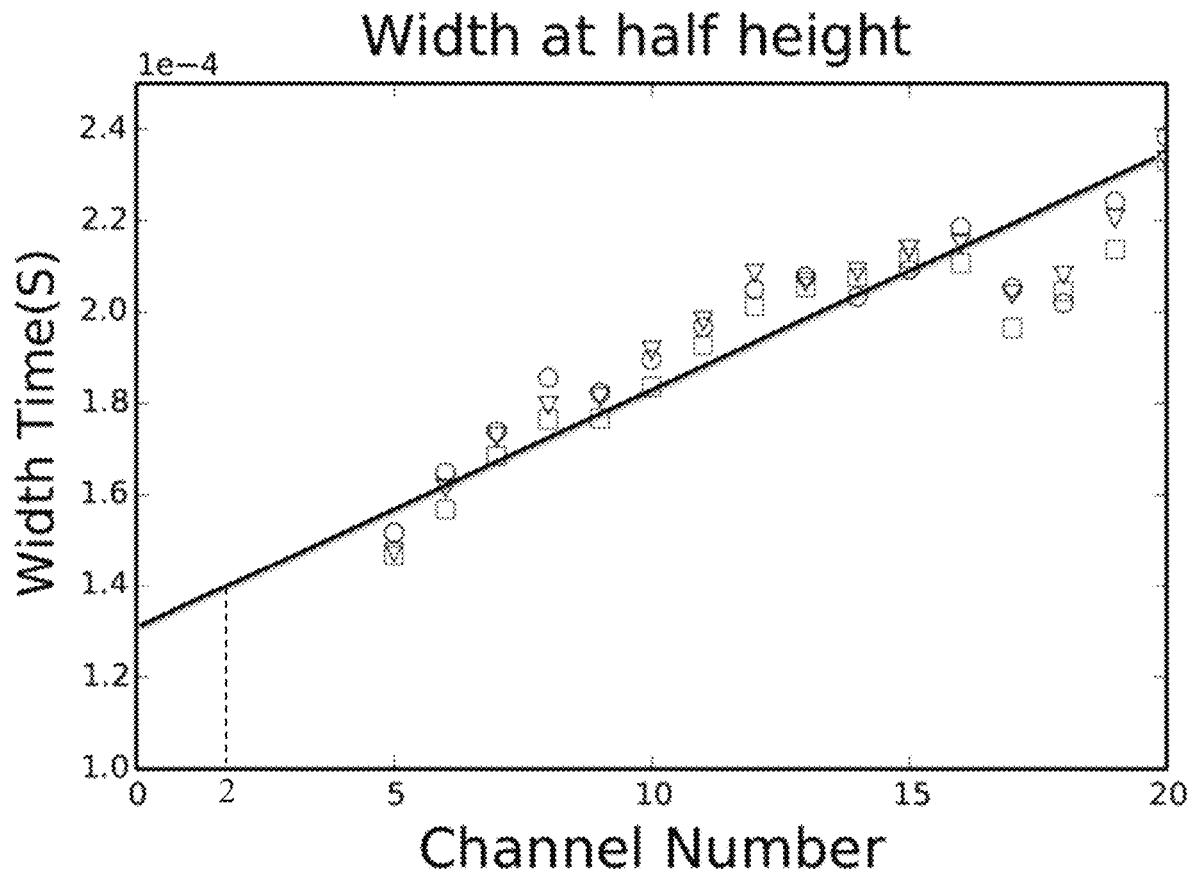
FIG. 16a is a plot of the sheep orthodromic responses' N1 peak width at half height as a function of the channel number.
Figure 16B:
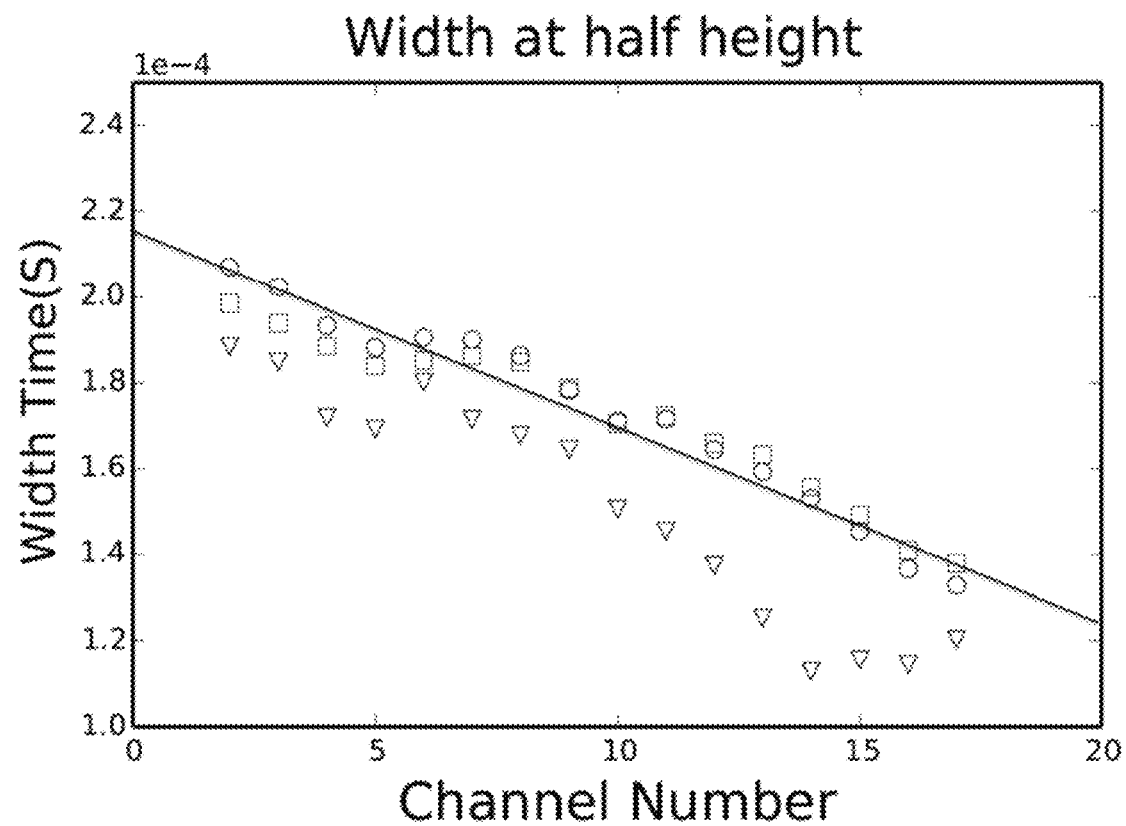
FIG. 16b is the corresponding plot for antidromic responses.

The ECAP peak width, defined here as the width at half height of the observed N1 peak, was determined on all channels, at various stimulation current levels. FIG. 16*a* is a plot of the sheep orthodromic responses' N1 peak width at half height as a function of the channel number for stimulation currents of 1 mA (squares), 0.9 mA (circles) and 0.8 mA (triangles). FIG. 16*b* is the corresponding plot for the antidromic responses' N1 peak width at half height as a function of the channel number, for stimulation currents of 1.106 mA (squares), 0.996 mA (circles) and 0.801 mA (triangles). Raw neural response measurement data was interpolated in order to remove sampling quantisation effects and improve the estimates of peak width. In each plot the straight line is from least squares fit of the data for all the measurements averaged for each channel. FIG. 16 shows that the relationship of the width at half height of the responses with the channel number is substantially independent of the stimulation current. Thus the approach of extrapolating such data to the stimulus channel location (channel 2) is robust to variations in stimulation current and/or to movement induced changes in the recruitment efficacy of a given current.

In FIG. 16 the width at half height (HH) of the responses in the orthodromic direction have a slope with channel number of $5.2 \times 10^1$, and in the antidromic direction the slope is $5.5 \times 10^{-6}$, which demonstrates that the fibres which are responding in both antidromic and orthodromic directions have similar distributions of fibre diameters.

In FIG. 16*a* the stimulus channel is channel 2 so that the originating state of stimulation of interest in this embodiment is the peak width at channel 2. Extrapolating the channel 5-20 orthodromic data back to the site of channel 2 gives an estimated channel 2 peak width of 0.00014 s (140 μs). In FIG. 16*b* the stimulus channel is channel 20 so that the originating state of stimulation of interest in this embodiment is the peak width at channel 20. Extrapolating the channel 2-17 antidromic data back to the site of channel 20 gives an estimated channel 20 peak width of 0.000125 s (125 μs). Taking the average of the orthodromic estimate and the antidromic estimate, and comparing to FIG. 10, allows the average electrode-to-fibre distance along the array to be estimated at about 5 mm.

Figure 17:
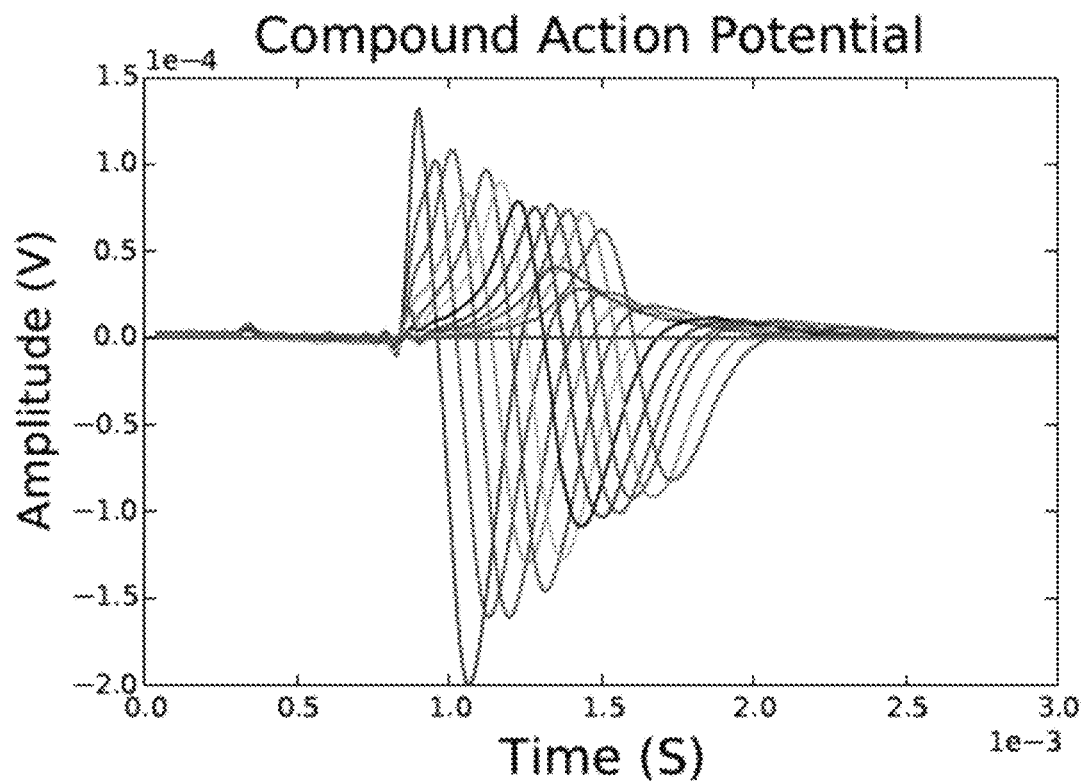
FIG. 17 is a plot of ECAPs recorded from electrodes placed in the sheep epidural space.
Figure 18:
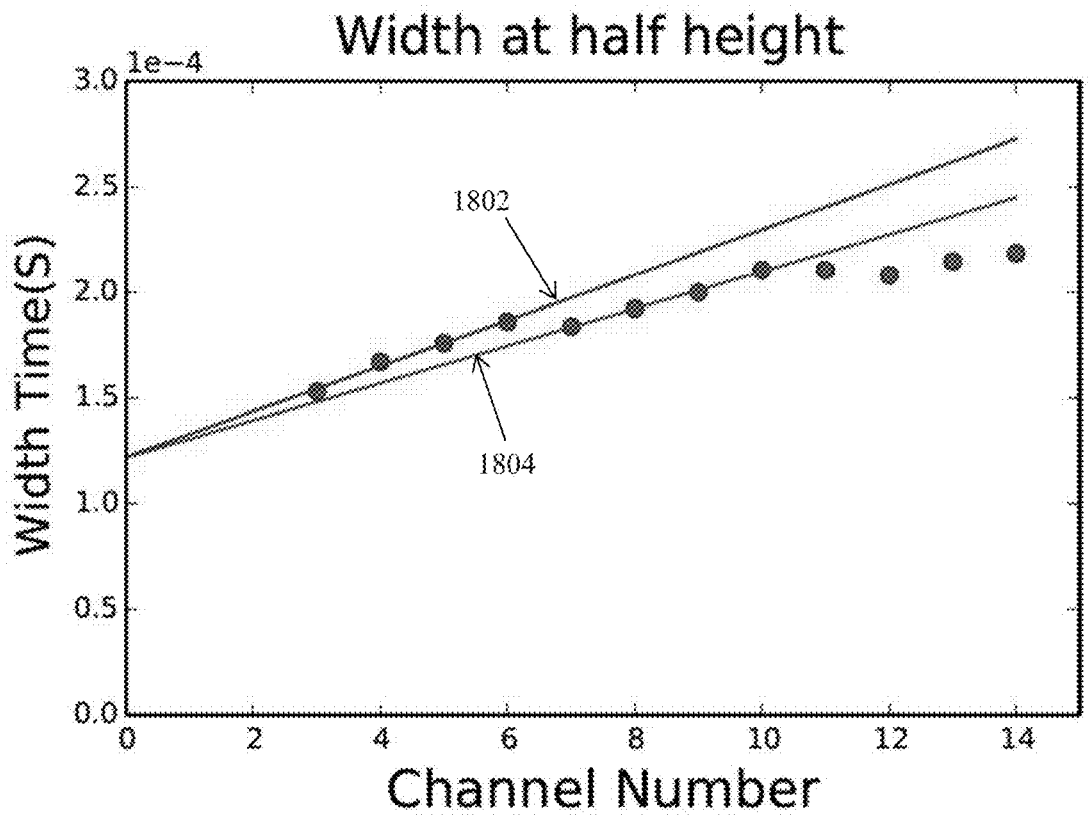
FIG. 18 is a plot of the width of the N1 peak plotted against the recording channel number, from the data of FIG. 17.
Figure 19A:
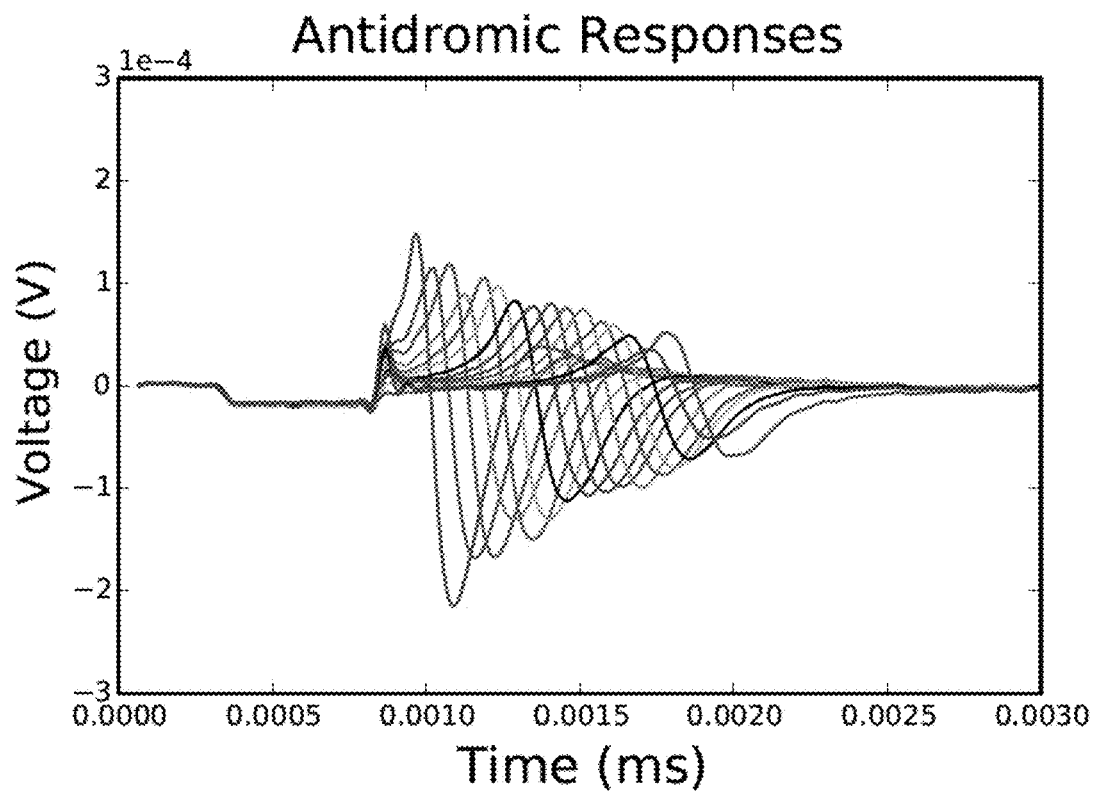
FIGS. 19a and 19b are plots of ECAPs recorded from 24 electrodes placed in the epidural space of another sheep, in the orthodromic and antidromic direction respectively.
Figure 19B:
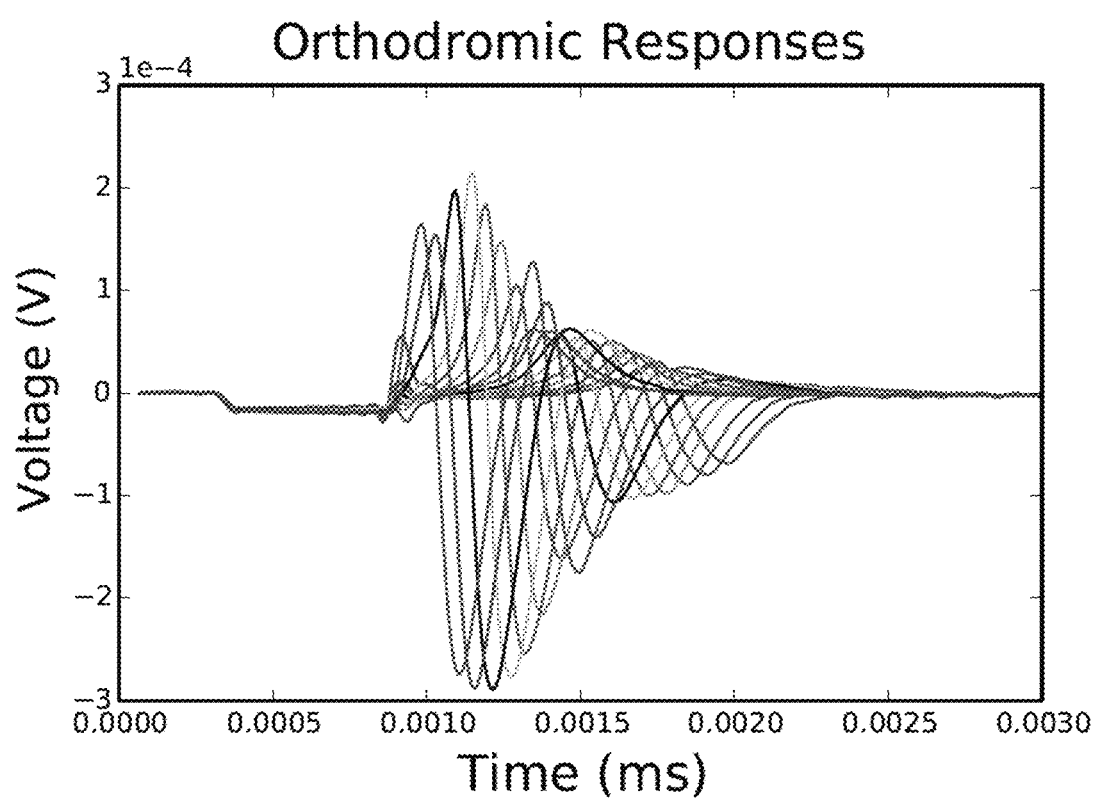
Figure 19C:
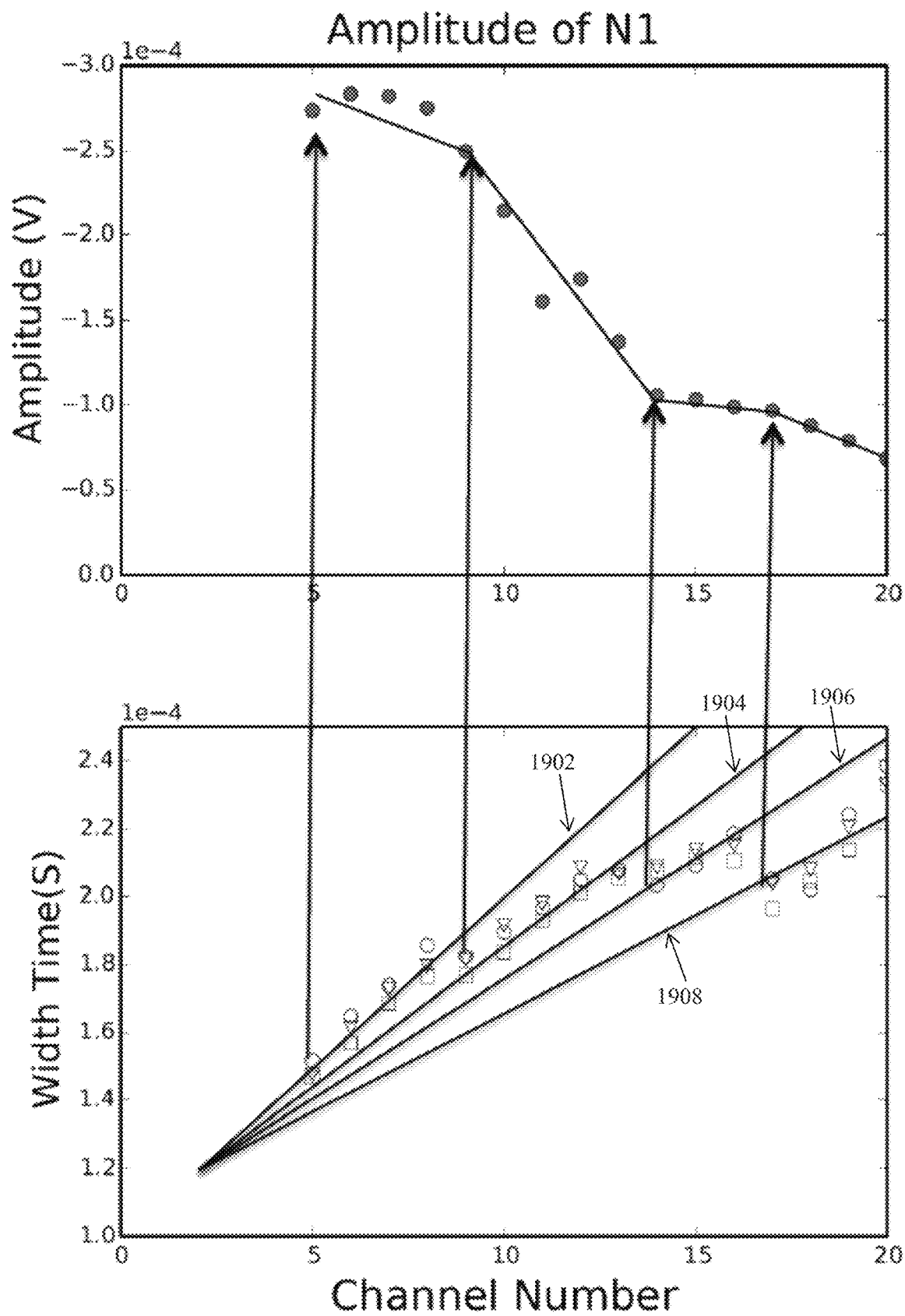
FIGS. 19c and 19d are plots of response amplitude and response peak width for the recordings of FIGS. 19a and 19b, respectively.
Figure 19D:
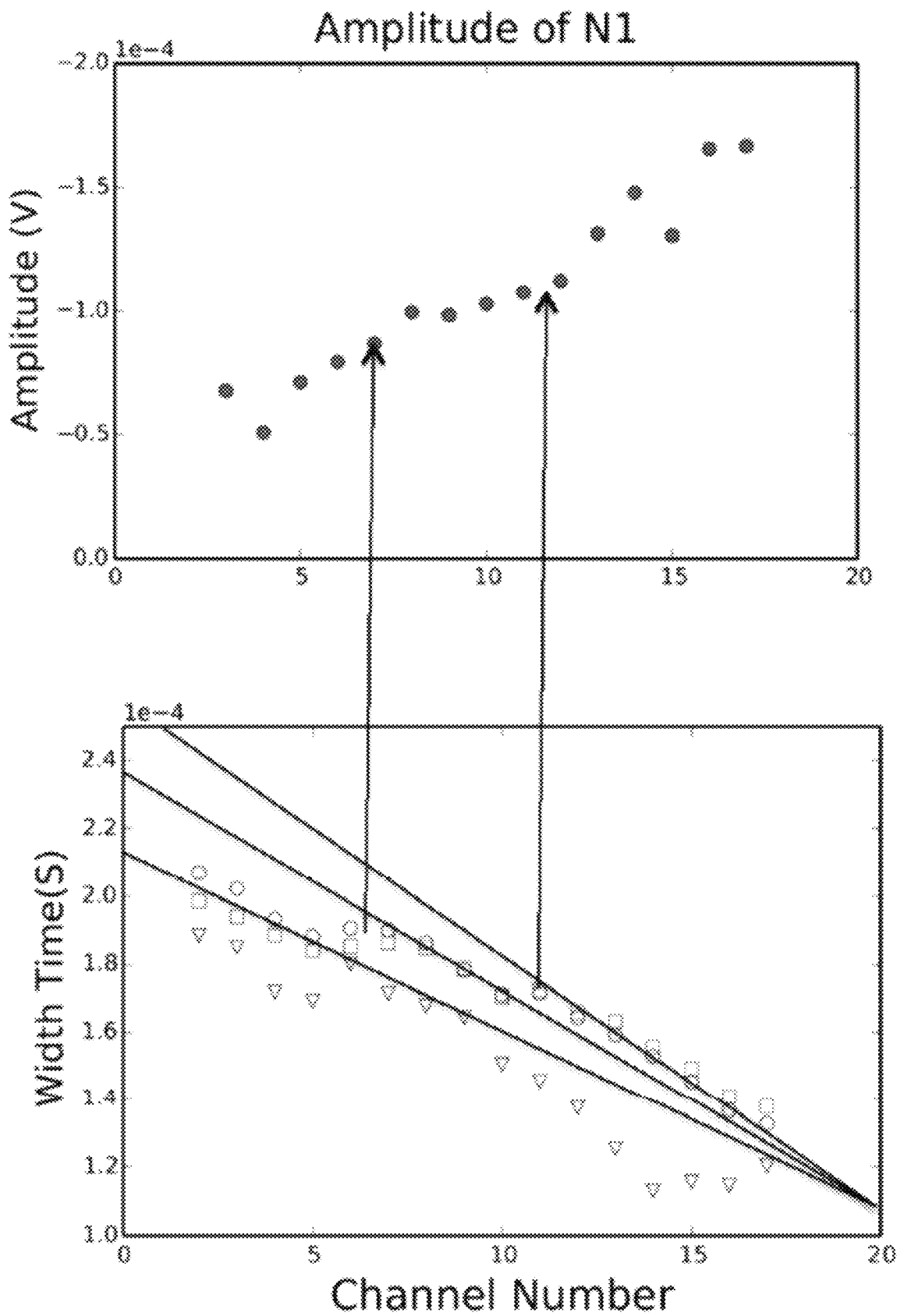

In another experiment ECAPs were recorded from electrodes placed in the sheep epidural space for a stimulation current of 1 mA 40 μs pulse width biphasic stimuli. The wave form measured on a single electrode has a duration of less than 1.5 ms and the recordings on electrodes which are a short distance from the stimulation electrode are truncated by the blanking period of the amplifier and presence of the stimulus current. FIG. 17 shows the obtained recordings. FIG. 18 is a plot of the width of the N1 peak plotted against the recording channel number, from the data of FIG. 17. As shown by fitted line 1802, the width of the N1 peak is linear with the propagation distance across the first 4 electrodes (channels 3-6). As shown by fitted line 1804 the width of the N1 peak is also linear for the next four electrodes (channels 7-10) albeit with a different, smaller, slope. A corresponding fitted line could be fitted to the final few electrodes, channels 12-14. The y-intercept of lines 1802 and 1804 is, notably, the same: 0.12 ms (120 μs). This represents the width of the ECAP if it could be recorded under the stimulating electrode. Some embodiments of the invention may thus fit a plurality of lines to the ECAP width or dispersion measurements, being one line fitted to each subset of electrodes positioned within each respective vertebral segment. Such embodiments reflect the fact that discontinuities in dispersion appear with propagation distance, accompanied by a change in the slope of the dispersion towards smaller slopes, due to the removal of smaller diameter slower conducting fibres from the recruited population as such fibres terminate at each crossing between vertebral segments. In such embodiments the plurality of fitted lines may each be extrapolated to the stimulus location to estimate the originating peak width, and/or the fitting of such lines may be constrained by a requirement that each line must intersect all others at the stimulus channel, to thereby improve the robustness of the multi-line fitting estimate of the originating state of stimulation, as compared to a single line fitting. In FIG. 18 it can be seen by visual inspection that channel 11 most likely is adjacent a vertebral segment crossing in a region where only a subset of that segment's terminating fibres have in fact terminated, so that channel 11 is not clearly grouped with either channels 7-10 nor channels 12-14. Some embodiments may seek to identify and discard such vertebral segment crossing data points when fitting lines 1802, 1804, etc.

To further study this effect a 24 channel electrode was implanted in another sheep and antidromic and orthodromic responses were measured, with results shown in FIG. 19. Stimulation was tripolar, biphasic. For FIG. 19*c* stimulation was delivered from a cathode on electrode 2 and anodes on channel 1 and 3, and recording electrodes from 5 to 20. For FIG. 19*d* stimulation was delivered from a cathode on electrode 20 and anodes on channel 19 and 21, and recording electrodes from 2 to 17. FIGS. 19*c* and 19*d* show that the discontinuities in the dispersion which appear with the propagation distance arise in both the orthodromic and antidromic conduction directions, consistent with the neuroanatom of the spinal cord. The present technique may thus be used to assess electrode height not only when stimuli are delivered at the caudal end of the array, but also when stimuli are delivered at the rostral end of the array. When stimuli are delivered from part way along the array, recording electrodes positioned both caudally and rostrally of the stimulus electrode(s) may be used to provide both orthodromic and antidromic estimates of ECAP dispersion to give a combined estimate of the originating ECAP peak width and the electrode height. In the study of FIG. 19 there were 4-5 electrodes spanning a single vertebral segment and recordings were made across 4 vertebral segments. It is evident when comparing the upper and lower portions of FIG. 19*c*, and of FIG. 19*d*, that both the dip or cornerpoint in the amplitudes and the change in slope of the dispersion plot correspond with the fibres crossing from one verterbral segment to the other. The data points indicated by triangles, squares and circles in the lower plots of FIGS. 19*c* and 19*d* reflect dispersion data obtained in response to stimuli of differing amplitude. Fitted lines 1902, 1904, 1906 and 1908 correspond to each vertebral segment and, despite having different slope, each have the same value at the stimulus electrode, channel 2. The multiple lines fitted to the antidromic data of FIG. 19*d* also have a shared intercept at the stimulus electrode on channel 20, around 0.11 ms, allowing response peak width at the site of the channel 20 stimulus to be robustly estimated, and in turn allowing relative or absolute electrode-to-nerve separation to be measured as discussed elsewhere herein.

Thus, the above approach allows an absolute value of the electrode-to-fibre distance to be estimated solely from electrical ECAP measurements.

Figure 20:
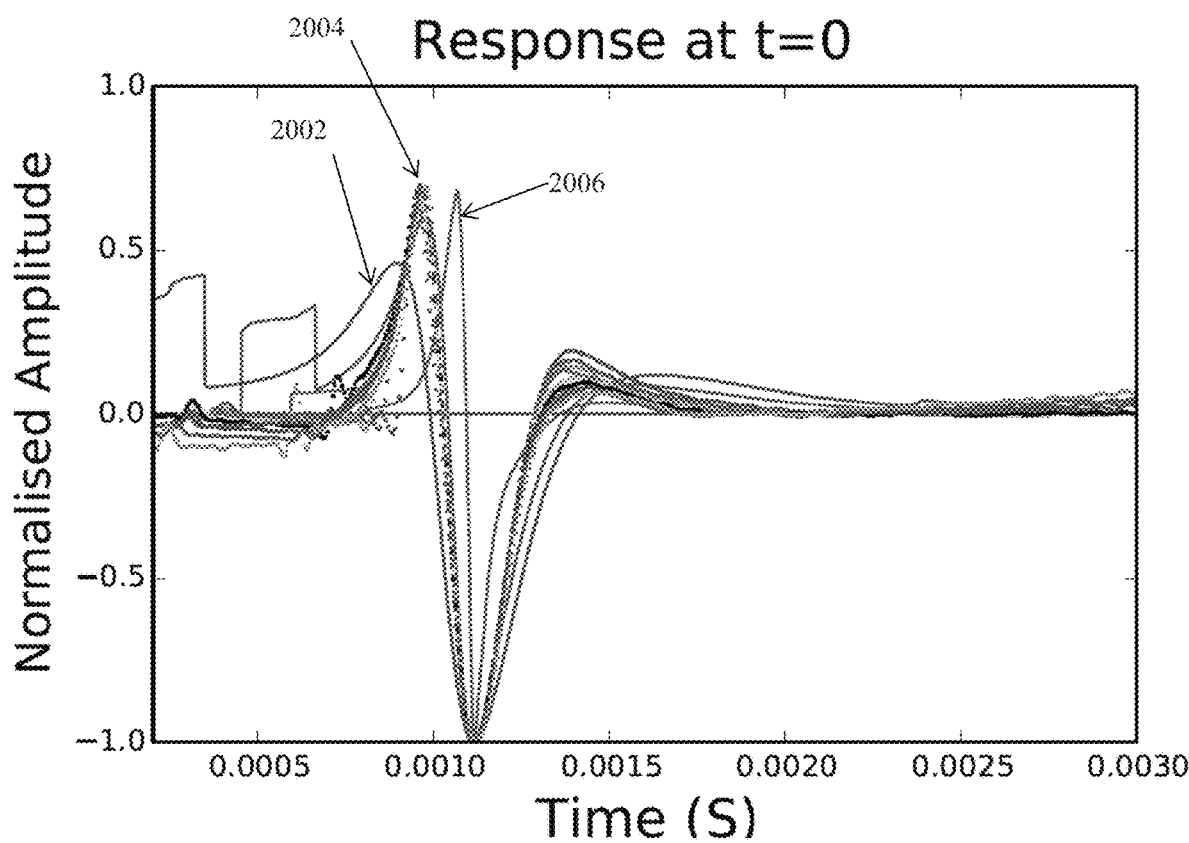
FIG. 20 plots simulated ECAPs produced at varying nerve-to-electrode separation at the site of stimulation, together with experimental data transformed to the site of stimulation.

To further test the validity of the 5 mm separation estimate obtained above in relation to FIG. 16, the theoretical "channel 0" responses evoked by an electrode positioned at 2 mm, 5 mm, 8 mm and from a nerve fibre were simulated. In FIG. 20, the continuous curve 2002 is the simulated response at 2 mm separation, continuous curve 2004 is the simulated response at 5 mm separation, and 2006 is the simulated response at 8 mm separation. The experimental data points shown in FIG. 20 are produced by taking the experimental data of FIG. 15*a*, time scaling each channel's observed response to have a peak width equal to the experimentally determined "channel 0" peak width, removing the pre-response latency at that electrode as defined by conduction velocity and electrode distance from the stimulus site by temporally aligning the N1 peak of each response, and normalising the N1 amplitude. As can be seen in FIG. 20, the experimentally observed responses when scaled in this manner (a) take substantially the same profile as each other, and (b) coincide very closely with the simulated channel 0 response 2004 which is evoked by the simulated electrode when at a 5 mm spacing from the fibre, thereby verifying the estimate of 5 mm produced above.

Another embodiment of the invention further recognises that FIGS. 6-14 reveal a means by which the size distribution of fibres recruited by a single stimulus may be estimated from ECAP measurements. Referring to FIGS. 11 and 12, it can be seen that for a given fibre population distribution, the observed slope of the ECAP peak width depends on electrode-to-fibre distance, the slope being larger when the distance d is smaller.

A further variable which affects the dispersion, or growth in peak width, is the conduction velocity of the recruited fibre. However the conduction velocity can be determined from the latency of the measured responses as is visible in FIG. 15a in which the velocity of the N1 peak is 116 ms$^{-1}$. The SFAP which conducts at this velocity in the model has a diameter of 21 μm, which is consistent with the diameter versus conduction velocity slope of 5.4 which has been reported.

Figure 21:
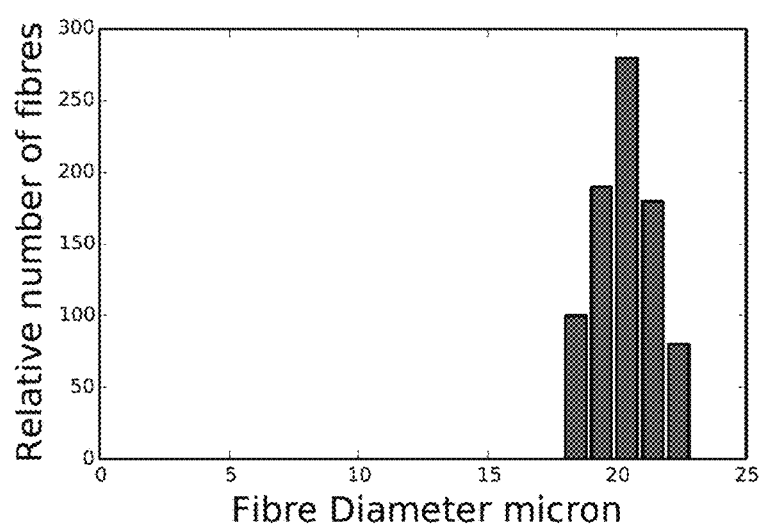
FIG. 21 illustrates a best-fit fibre size distribution profile.
Figure 22:
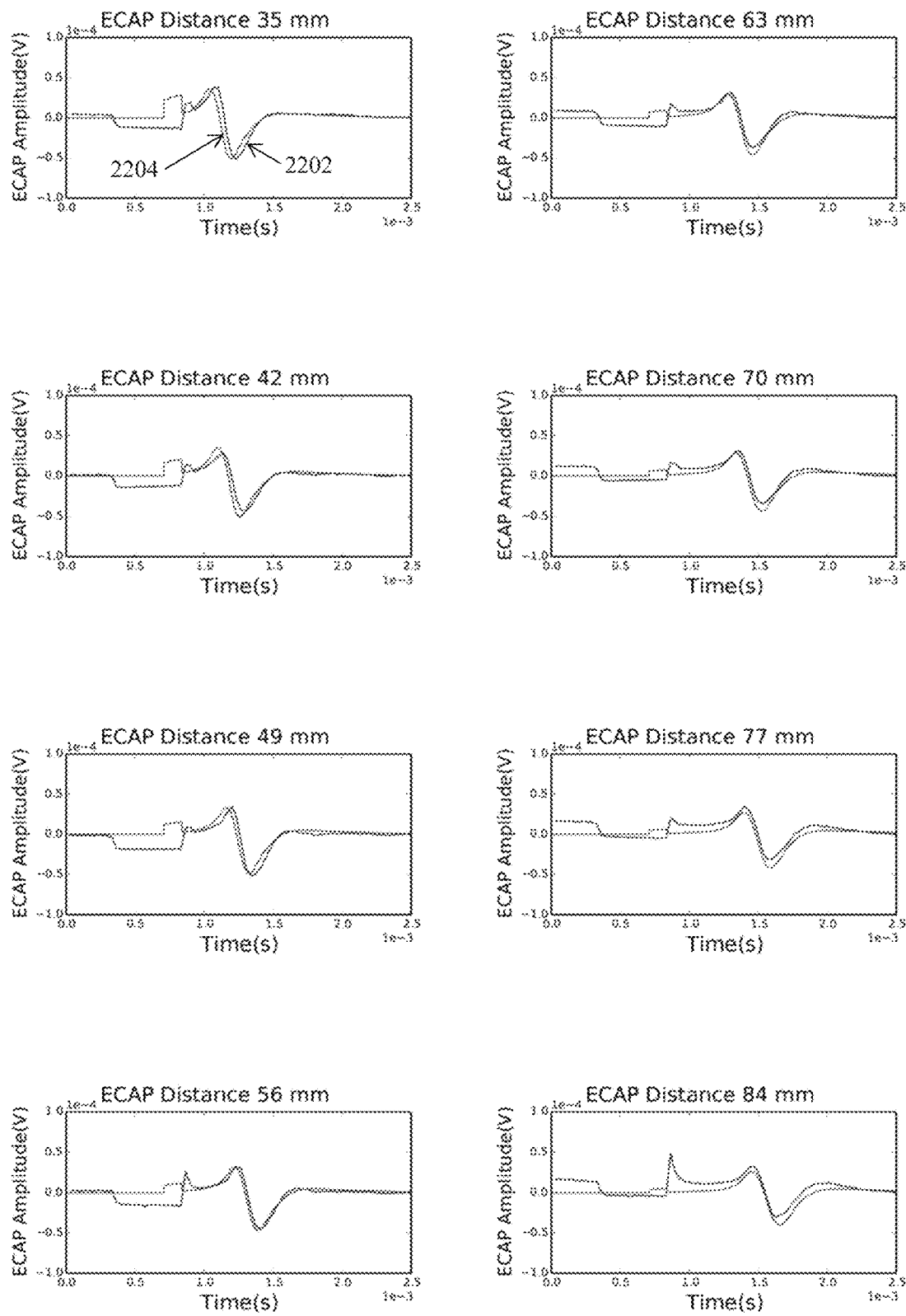
FIG. 22 illustrates a synthetic ECAP modelled from the distribution profile of FIG. 21, together with observed sheep ECAP profiles, at various distances from the stimulus site.

Thus, the conduction velocity observed in FIG. 15a enables a determination to be made as to the diameter of the most abundant fibre in the recruited fibre population, in this case 21 μm. Next, the slope of the width at half height observed in FIGS. 16a and 16b enables the relationship shown in FIG. 12 to be used to estimate the distribution of recruited fibres. Finally, a profile of the distribution of recruited fibres may be produced. This involves taking a nominal distribution profile, and summing the individual fibre contributions to a simulated ECAP using a chosen single fibre model, and fitting the simulated ECAP to an observed ECAP by trial and error adjustment of the nominal profile, until a best fit is found. In the case of the sheep data of FIG. 15a, the best fit fibre distribution profile determined in this manner is shown in FIG. 21. FIG. 22 comprises plots 2202 of the simulated ECAP resulting from single fibre modelling and summation of a recruited fibre distribution having the profile shown in FIG. 21, together with plots 2204 of the actual observed sheep ECAP data, as observed at electrodes at distances from 35 mm to 84 mm away from the stimulus site. As can be seen, the best fit fibre distribution profile of FIG. 21 when simulated results in a close fit of the simulated ECAP 2204 to the observed sheep ECAP 2202, and such fitting thus enables the fibre distribution profile to be estimated. Any suitable fitting technique, such as a pointwise least squares fitting, may be applied to determine which nominal fibre distribution profile gives the best fit to an observed ECAP.

Accordingly, some embodiments of the invention may additionally or alternatively seek to use response dispersion to estimate the recruited fibre population's dominant fibre size, and also the width of the distribution of fibre sizes recruited.

Thus the response of the sheep spinal cord to SCS demonstrates a consistent increasing distribution of fiber velocities with increasing current. These techniques are also applicable to use in humans, where detailed understanding of the electrophysiological response of the spinal cord to electrical stimulation, and the distribution of fiber diameters in chronic pain sufferers, may lead to better diagnostic and patient programming outcomes.

Figure 23:
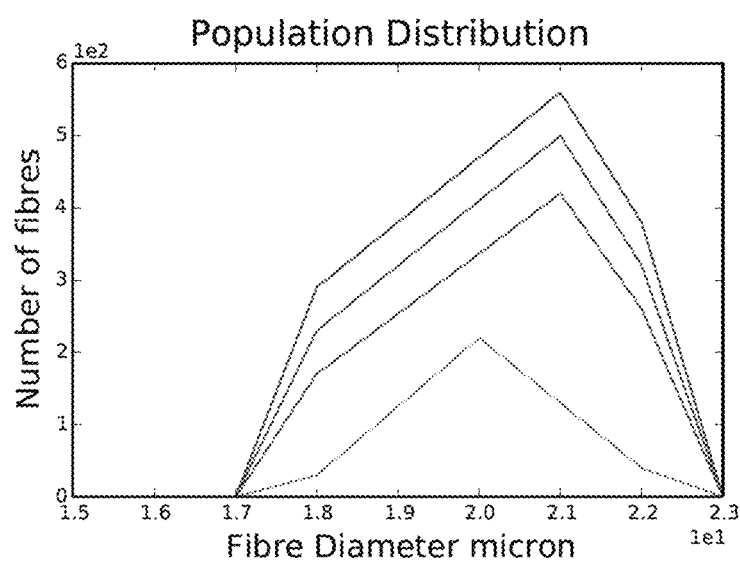
FIG. 23 illustrates best fit distribution profiles determined for sheep ECAPs observed in response to four different stimulus current levels.

The effect of increasing the stimulation current, as observed in FIG. 15b, on the profile of the best-fit distribution was also determined. The best fit distribution profiles determined for each current level are shown in FIG. 23. FIG. 23 shows that the population of responding fibres varies with the changes in current, and in particular as the current is increased the proportion of smaller diameter (18-19 μm) fibres contributing to the ECAP is expected to increase.

Moreover, once the fibre distribution characteristics are known, including the dominant fibre size recruited (in FIG. 23 being 20-21 μm), distribution width (17-23 μm) and distribution profile (as shown in FIG. 23), single fibre modelling and summation even enables the number of fibres of each size which are being recruited to be estimated, by amplitude comparison to the observed ECAP. Thus, as shown in they-axis of FIG. 23 it can be determined for the sheep data that at peak current about 300 18 μm fibres were recruited and about 550 21 μm fibres were recruited, for example. Similarly, the total number of fibres recruited is simply the integral of the population distribution curve and for the sheep spinal cord the total number of recruited fibres is 2080 fibres at 1.0 mA, 1780 fibres at 0.9 mA, 1440 fibres at 0.8 mA and 545 fibres at 0.7 mA.

In yet another embodiment, a technique which can be used to estimate the nerve-to-electrode distanced involves probing the Rheobase by delivering appropriate stimuli and measuring the neural responses thereto.

Figure 24:
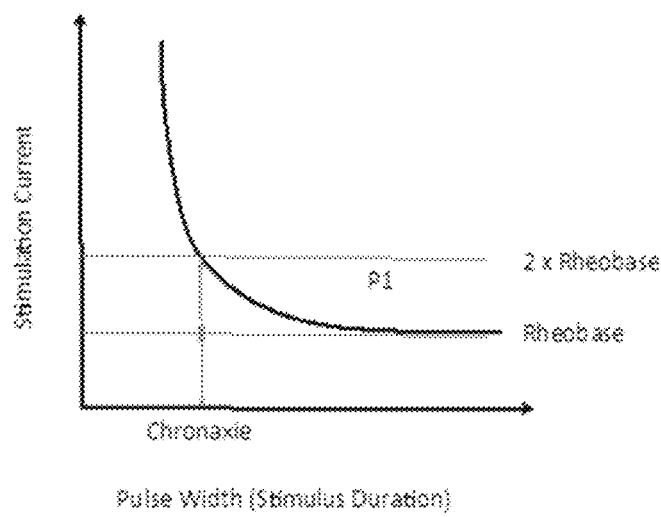
FIG. 24 illustrates a strength-duration curve.

A plot of the threshold current required to evoke a response against the pulse width is a strength duration curve as shown in FIG. 24. The Rheobase current is defined as the maximum current at infinite pulse width which doesn't evoke a response. The present embodiment recognises that the Rheobase current depends on the separation of the electrode from the nerve, so that the curve of FIG. 24 shifts towards the origin for a small separation, and shifts away from the origin (up and to the right in FIG. 24) for larger separations.

Figure 25:
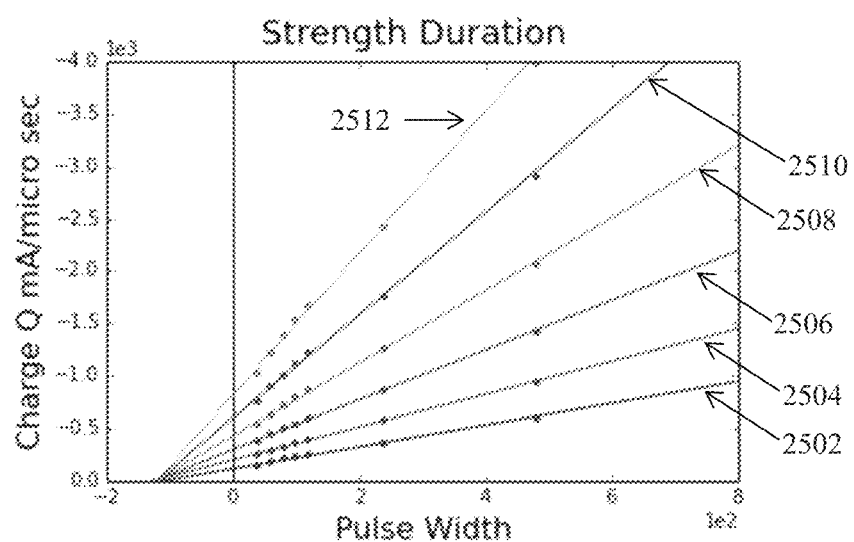
FIG. 25 illustrates an alternative representation of the strength duration curve, for varying electrode-to-nerve separation.

FIG. 25 comprises an alternative representation of the strength duration curve of FIG. 24, by plotting applied charge against pulse width, for a 10 micron diameter fibre. Further, this figure includes a plot at a number of electrode separations from the fibre, namely a plot 2502 for a separation of 3 mm, 2504 for 4 mm, 2506 for 5 mm, 2508 for 6 mm. 2510 for 7 mm and 2512 for 8 mm. In this representation of the strength duration curve, each curve is substantially linear and the slope is equal to the Rheobase current.

Figure 26:
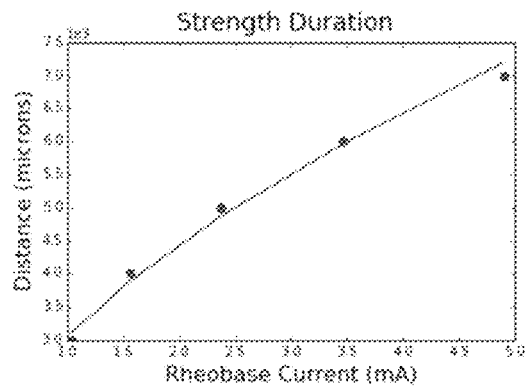
FIG. 26 is a plot of the Rheobase current against electrode to fibre separation.

FIG. 25 allows a plot, shown in FIG. 26, to be derived which represents the relationship of the Rheobase current R to the separation h from the fibre. In this instance of a simulated single fibre diameter, the fitted relationship is $R=Bh^A$, where A and B are empirically fitted constants. Here A=0.5385 and B=10e3.485.

This process by which FIG. 26 was obtained for a single fibre model of a fibre diameter of 10 microns was then repeated for multiple fibre diameters D, namely D=[7,8, 9.10,11,12] microns. For these single fibre sizes, the fitting constants A were respectively calculated as taking the values A=[0.55,0.537,0.532.0.5385,0.53,0.51]. This indicates that A is approximately constant with changing fibre diameter at least throughout this range, the average value of A being 0.5329.

Figure 27:
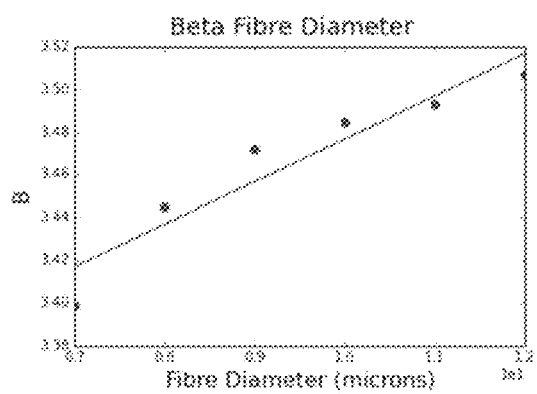
FIG. 27 is a plot of a Rheobase-to-height fitting constant against fibre diameter.

On the other hand, the fitting constants B were respectively calculated as taking values B=13.399.3.445,3.472, 3.485,3.493,3.5071. This indicates that B is monotonic increasing with increasing fibre diameter, at least in this fibre diameter range. FIG. 27 plots the values of B against fibre diameter, and also shows a straight-line-fit to the data points, having the equation B=0.01991 D+3.278, where D is the diameter of the fibre.

Thus, this embodiment applies stimuli of varying pulse width from a first stimulus electrode to determine at least two points on the strength-duration curve, as it exists for the unknown separation h. From two such points, the Rheobase R for the first-recruited fibre can be calculated in respect of the first stimulus electrode. Because fibre diameter D is unknown, the Rheobase R alone does not yield h.

Figure 28:
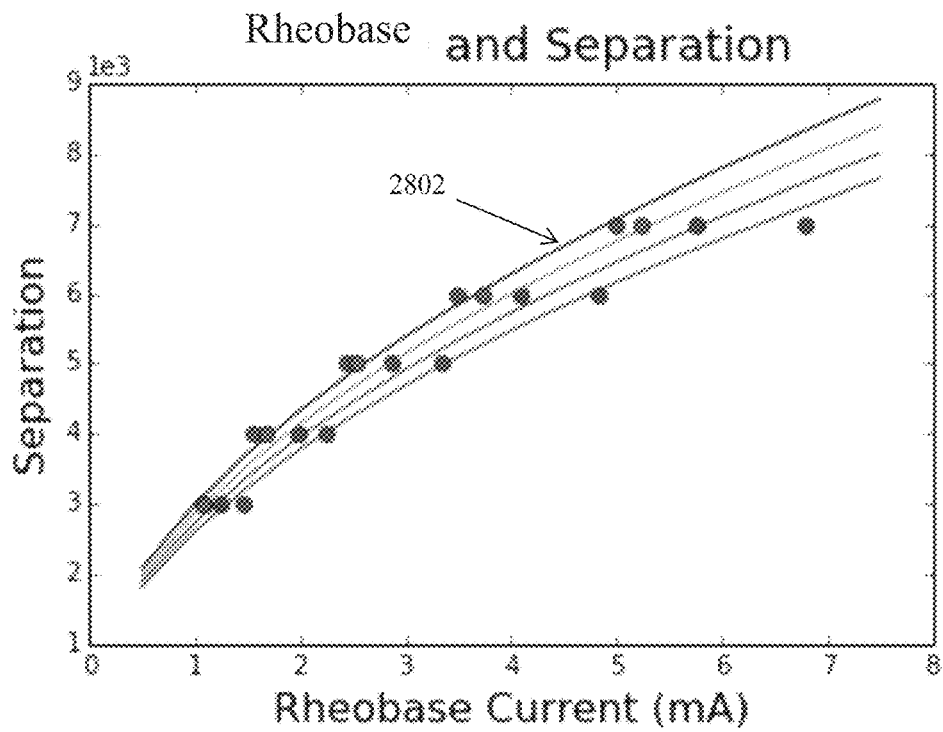
FIG. 28 presents simulated plots of the relationship of increasing separation upon Rheobase.

FIG. 28 shows simulated plots of the relationship of increasing separation upon the expected Rheobase value. As expected, Rheobase generally increases as electrode-to-nerve distance increases. However, for each single fibre diameter, the relationship follows a curve and not linear, and moreover at any given separation the Rheobase value of one fibre diameter differs from a differing fibre diameter. As the observed response is a compound action potential, at any given separation the first-recruited fibre will always be the same, being the largest most proximal fibre to the stimulus electrode. That is, the separation vs Rheobase relationship for the observable compound response will be the same as the curve 2802 of the largest most easily recruited fibre.

The present embodiment thus further provides for determining a conduction velocity of the evoked response at threshold, as conduction velocity is well related to fibre diameter. For example two sense electrodes spaced apart along a neural pathway may record a time of arrival of an evoked response in order to determine the conduction velocity V. The recruited fibre diameter D can then be determined by the empirically determined relationship $D=V/X$, where X is typically ascribed a value around 5.4-6. Knowing D, B can be deduced from FIG. 27. Now knowing R, B and A, the equation $R=Bh^A$ can be solved to give the electrode to fibre separation h, as desired. In this embodiment the originating state of stimulation is thus the Rheobase, for which an observable characteristic is defined by a single fibre size as demonstrated by reference to FIG. 28.

In other embodiments, rather than a straight line fit, a curve may be fitted to the data points of FIG. 27 to improve B estimation, and such embodiments are within the scope of the present invention.

Figure 29:
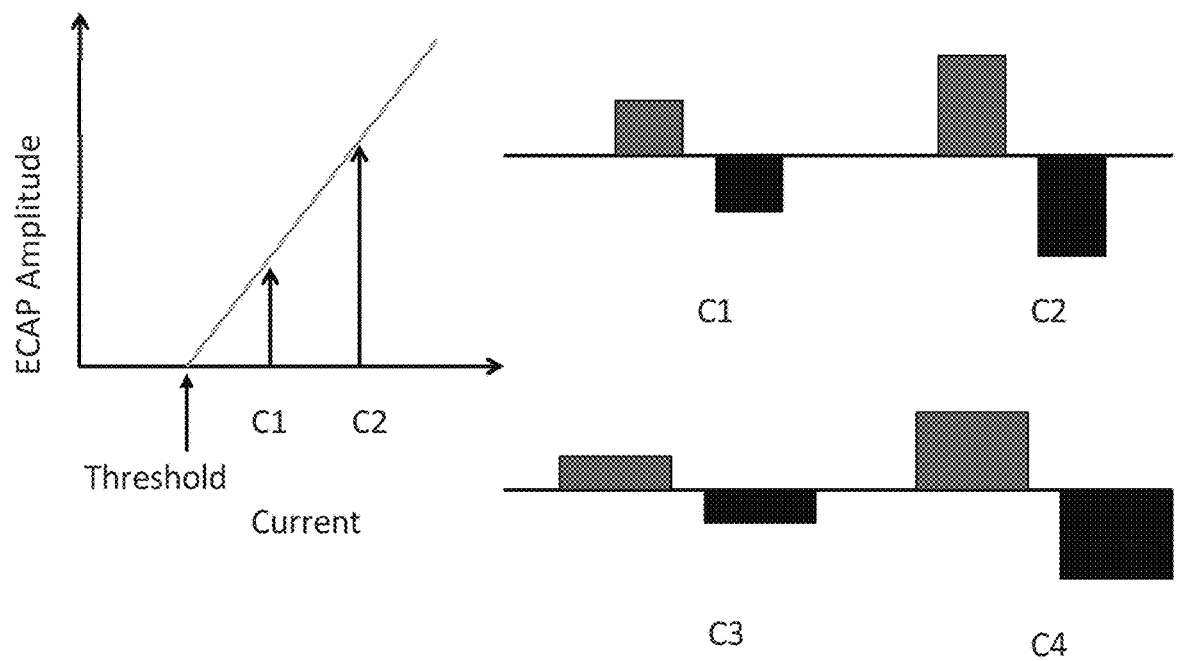
FIG. 29 schematically depicts Rheobase measurement.

There are a number of ways to measure the Rheobase dynamically and in real time such as during SCS. As described previously the Rheobase current can be estimated from the slope of the charge duration curve. The slope estimation requires at least two points along this curve, and to obtain these two points requires estimation of the threshold of response for two different stimulus durations. The threshold measurement can be made in a number of ways, and a simple way to make this measurement, schematically depicted in FIG. 29, is to measure the slope of the amplitude of the ECAP with respect to stimulation current, to estimate a threshold current. Determination of the threshold at two pulse widths provides the data necessary to compute the Rheobase current. Thus in this method four stimuli are required, but at least two of the stimuli can be controlled to have the same charge as a required therapeutic level, and thus provide therapeutic stimuli. The other two stimuli required to complete the Rheobase measurement can then be lower in amplitude and thus not uncomfortable and may even be below a perception threshold.

It is to be appreciated that the stimuli sequence could be applied continuously and the Rheobase calculated continuously and averaged over time, or further signal processing techniques applied to improve the SNR of this measure. The conduction velocity needs only be measured infrequently and for many applications can be measured only once, or on rare occasions, to provide the remaining constant.

Figure 30A:
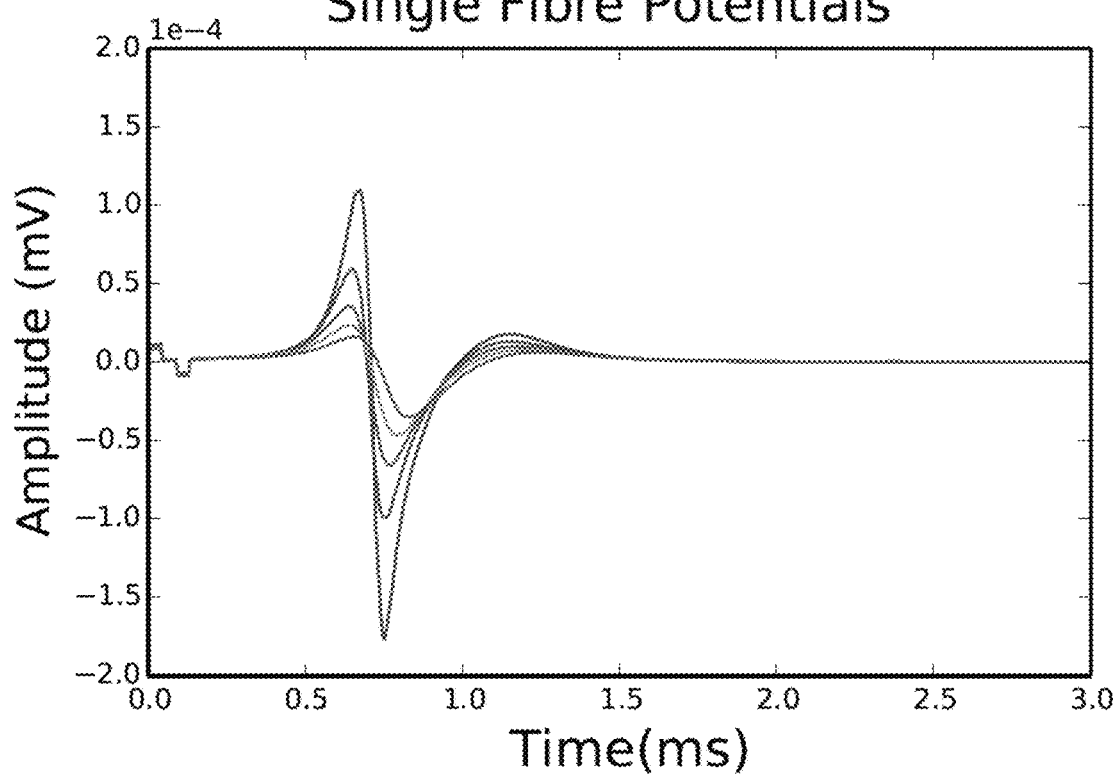
FIGS. 30a-30d illustrate another embodiment in which electrode-to-nerve separation is measured by extracting frequency components of neural measurements.
Figure 30B:
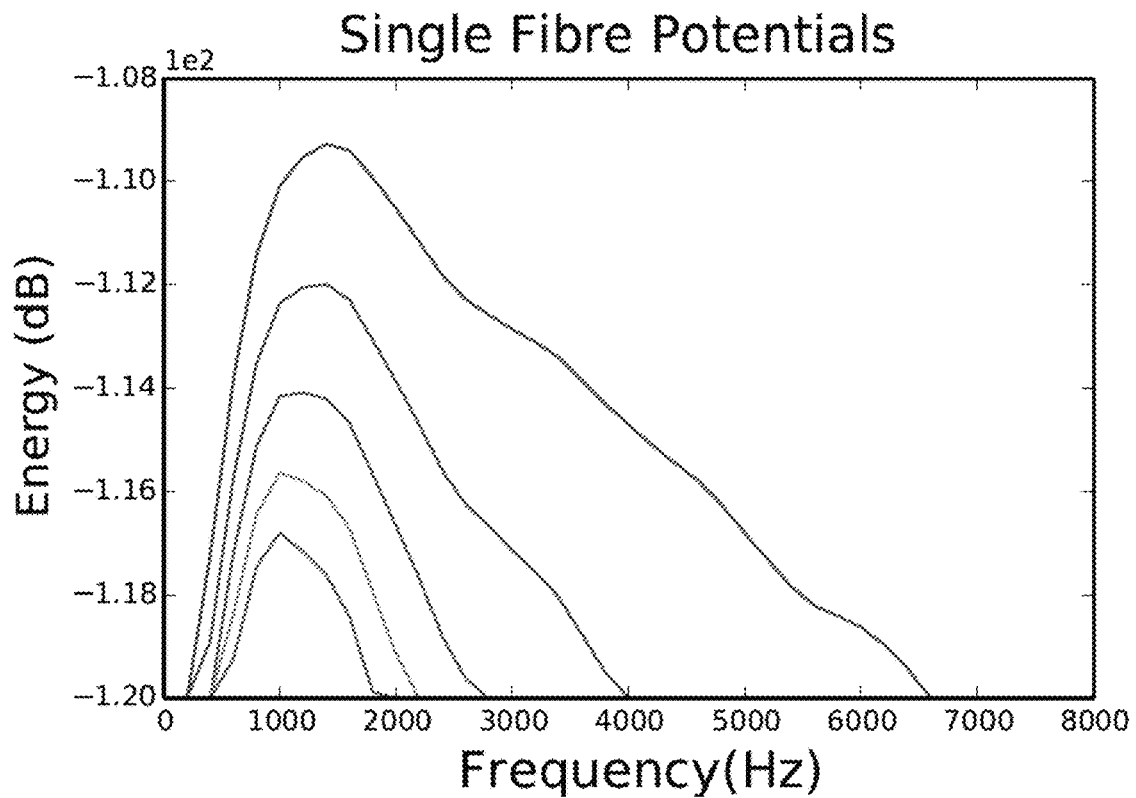
Figure 30C:
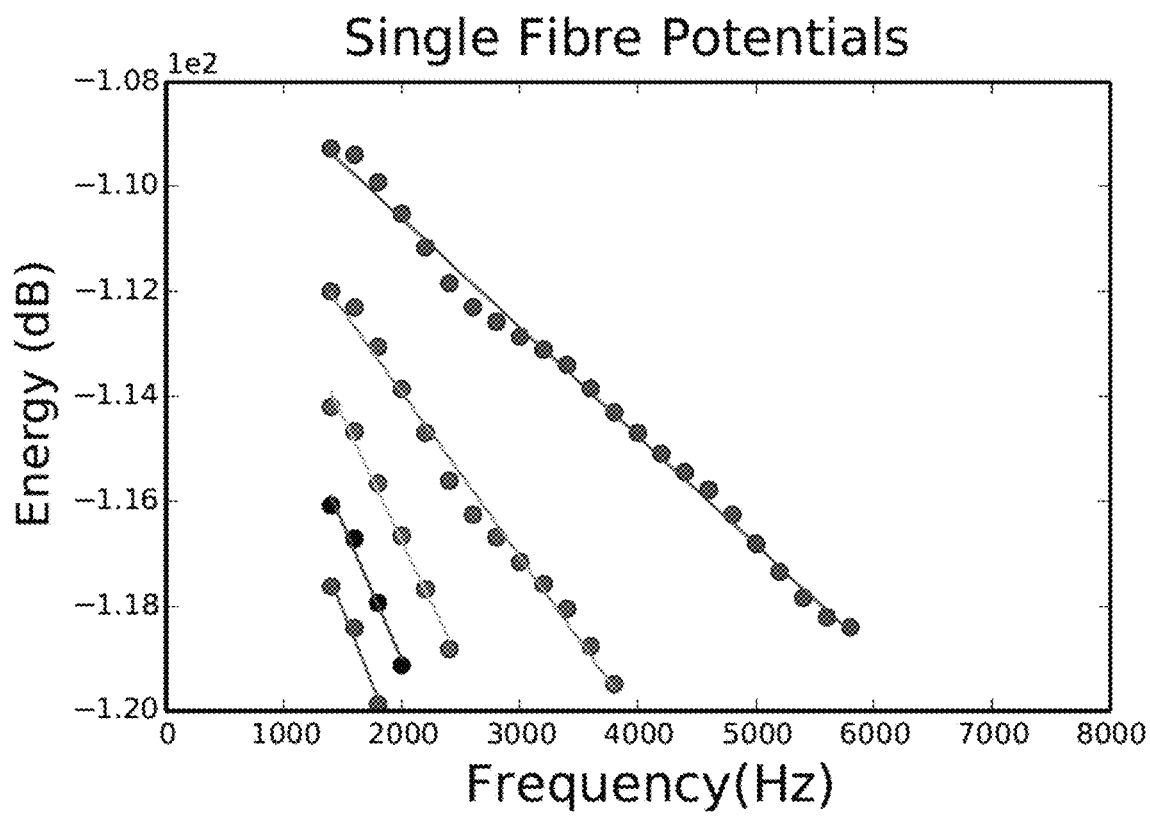
Figure 30D:
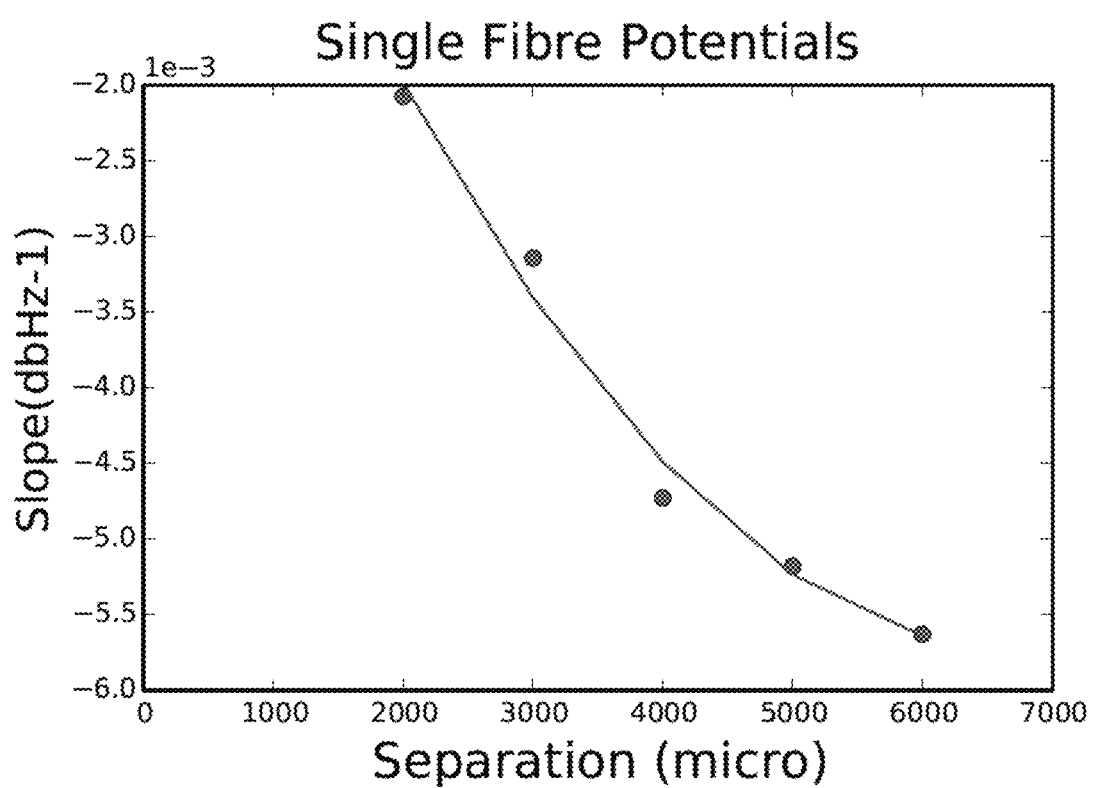

FIGS. 30a-30d illustrate another embodiment of the invention, in which ECAP dispersion, and electrode-to-nerve separation, are measured or assessed by extracting frequency components of the neural measurements, by fast Fourier transform. The neural measurements are first windowed to exclude discontinuities or like stimulus effects and/or measurement effects. The frequency domain information of the respective neural measurements may then be used to extract a measure of the dispersion. FIG. 30a plots simulations of the ECAP of a 12 µm diameter fibre measured 35 mm away from the stimulating site and at separations of 2,3,4,5 and 6 mm, respectively, between the electrode and the fibre. Once again, both the amplitude and the dispersion of the observed response changes with separation, with larger separations producing smaller more dispersed responses. FIG. 30b shows the Fourier spectrum of the data from the first figure (Haming window). The present embodiment operates by noting that the decay in the frequency response of each observed ECAP at frequencies higher than the peak is linear. It is also noted that the peak amplitude of each curve in FIG. 30b, and the spectral spread of each curve, reflects the sharpness of the observed response, and either or both such measures may thus be used as a measure of the inverse of response dispersion. FIG. 30c shows the slope of the decay of frequency contributions to each respective observed response, at frequencies higher than the peak of the respective curve. The present embodiment further notes that the slope of the decay of each curve is proportional to the separation of the fibre from the electrode, whereby a steeper decay slope corresponds to greater dispersion and thus greater separation. FIG. 30d is a plot of decay slope against separation, indicating the monotonic nature of this relationship in the separations observed, and for example FIG. 30d may be reflected in a lookup table whereby the spectral decay slope observed in a given response may be used to look up electrode-to-nerve separation. Such embodiments may be advantageous in measuring dispersion in noisy neural measurements, as a frequency roll-off can be averaged or fitted over a relatively wide spectral range. Such embodiments may further be advantageous in enabling a measure of dispersion to be obtained without reliance on the amplitude of the ECAP, for example in embodiments where manual user feedback or automated feedback operates to control recruitment at a substantially constant level.

The stimulation electrodes and sensing electrodes in one embodiment are an array of electrodes. The stimulus location and the measurement location could be changed from one measurement to the next, such as by being scanned across the array with electronic switching means, and the Rheobase/distance computed in real time and from this a two dimensional picture of the underlying neural active elements and their location with respect to the electrodes of the array could be determined.

An image so produced could in turn be used to guide a surgical procedure, such as the removal of tissue with little or no response such as is performed in DREZ lesion surgery, or detection and removal of aberrantly responding tissue such as the removal of brain lesions responsible for focal origin epilepsy.

The geometry of the sensing stimulating electrodes need not be planar but may be circumferential to a neural structure such as those employed in cuff electrodes. Electrodes spaced around the circumference of a major nerve, for instance the vagal nerve could use the techniques described above to provide estimates as to the locations of individual fascicles within the nerve bundle. It is highly desirable to be able to address individual fascicles with stimulation and a knowledge of the fascicle geometry and arrangement could, via current steering or other means, provide selective stimulation The fascicles in major nerves do not run a linear course through the nerve. For example, examination of serial cross sections of the nerve at different positions along the nerve would reveal that individual fascicles at the centre of the bundle in one section could be found at the edges in another section. This observation, combined with the herein described techniques to map the separation of electrode to active tissue, could be used to choose effective electrodes or be used to appropriately place a cuff electrode on a nerve during surgery.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of estimating adistribution of fibres recruited by astimulus, the method comprising:
   applying a stimulus via a stimulus electrode;
   obtaining from at least two sense electrodes spaced apart along a neural pathway respective measurements of a compound action potential propagating along the neural pathway, wherein the compound action potential is an evoked compound action potential (ECAP) of the fibres recruited by the stimulus;
   determining a conduction velocity of the compound action potential from the latency between the measurements, and determining from the conduction velocity a dominant recruited fibre diameter;
   determining a rate of dispersion of the compound action potential between the sense electrodes, and determining from the rate of dispersion adistribution of diameters of the recruited fibre population.

2. The method of claim 1, further comprising determining the rate of dispersion from any one or more of: the observed ECAP peak width, the ECAP peak spacing, the ECAP zero crossings, the ECAP half-height peak width, and the ECAP spectral content.

3. The method of claim 1, further comprising treating a neurological condition by administering or modifying a therapy in a manner responsive to the determined distribution of diameters of the recruited fibre population.

4. The method of claim 1, further comprising treating a neurological condition by administering or modifying a therapy in a manner responsive to a change in the determined distribution over time.

5. A device for estimating adistribution of fibres recruited by astimulus, the device comprising
   at least one stimulus electrode and at least two sense electrodes, configuredto be spaced apart along a neural pathway;
   measurement circuitry for obtaining a neural measurement from each sense electrode; and
   a processor configured to apply a stimulus via the stimulus electrode, obtain from the at least two sense electrodes respective measurements of acompound action potential propagating along the neural pathway, wherein the compound action potential is an evoked compound action potential (ECAP) of the fibres recruited by the stimulus, determine a conduction velocity of the compound action potential from a latency between the measurements, determine from the conduction velocity a dominant recruited fibre diameter, determine a rate of dispersion of the compound action potential between the sense electrodes, and determine from the rate of dispersion a distribution of diameters of the recruited fibre population.

6. The device of claim 5, wherein the processor is configured to determine the rate of dispersion from any one or more of: the observed ECAP peak width, the ECAP peak spacing, the ECAP zero crossings, the ECAP half-height peak width, and the ECAP spectral content.

7. The device of claim 5, wherein the processor is further configured to treat a neurological condition by administering or modifying a therapy in a manner responsive to the determined distribution of diameters of the recruited fibre population.

8. The device of claim 5, wherein the processor is further configured to treat a neurological condition by administering or modifying a therapy in a manner responsive to a change in the determined distribution over time.

9. A non-transitory computer readable medium for estimating a distribution of fibres recruited by a stimulus, comprising instructions which, when executed by one or more processors, causes performance of the following:
   applying a stimulus via a stimulus electrode;
   obtaining from at least two sense electrodes spaced apart along a neural pathway respective measurements of a compound action potential propagating along the neural pathway, wherein the compound action potential is an evoked compound action potential (ECAP) of the fibres recruited by the stimulus;
   determining a conduction velocity of the compound action potential from a latency between the measurements, and determining from the conduction velocity a dominant recruited fibre diameter;
   determining a rate of dispersion of the compound action potential between the sense electrodes, and determining from the rate of dispersion a distribution of diameters of the recruited fibre population.

10. The non-transitory computer readable medium of claim 9, further comprising instructions which, when executed by one or more processors, cause determining the rate of dispersion from any one or more of: the observed ECAP peak width, the ECAP peak spacing, the ECAP zero crossings, the ECAP half-height peak width, and the ECAP spectral content.

11. The non-transitory computer readable medium of claim 9, further comprising instructions which, when executed by one or more processors, cause treating a neurological condition by administering or modifying a therapy in a manner responsive to the determined distribution of diameters of the recruited fibre population.

12. The non-transitory computer readable medium of claim 9, further comprising instructions which, when executed by one or more processors, cause treating a neurological condition by administering or modifying a therapy in a manner responsive to a change in the determined distribution over time.

* * * * *

UNITED STATES PATENT AND TRADEMARK OFFICE
CERTIFICATE OF CORRECTION

| | | |
|---|---|---|
| PATENT NO. | : 11,938,320 B2 | Page 1 of 1 |
| APPLICATION NO. | : 17/121545 | |
| DATED | : March 26, 2024 | |
| INVENTOR(S) | : Parker | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 236 days.

Signed and Sealed this
Eighth Day of October, 2024

Katherine Kelly Vidal
*Director of the United States Patent and Trademark Office*